United States Patent [19]

Shand et al.

[11] Patent Number: 5,902,796

[45] Date of Patent: *May 11, 1999

[54] BIOACTIVE FACTORS OF ALOE VERA PLANTS

[75] Inventors: David G. Shand, Irving; Kenneth Yates, Grand Prairie; D. Eric Moore, Richardson; Bill H. McAnalley, Grand Prairie, all of Tex.; Santiago Rodriguez, Miami, Fla.

[73] Assignee: Carrington Laboratories, Inc., Irving, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/532,060

[22] Filed: Sep. 22, 1995

Related U.S. Application Data

[63] Continuation of application No. 08/532,060, Sep. 22, 1995.

[51] Int. Cl.⁶ .................... A61K 31/715; A61K 35/78
[52] U.S. Cl. .................... 514/54; 424/195.1; 514/783; 536/123.1; 536/127; 536/128
[58] Field of Search .................... 424/195.1; 514/54, 514/783; 536/123.1, 127, 128

[56] References Cited

U.S. PATENT DOCUMENTS

| | | | |
|---|---|---|---|
| 4,735,935 | 4/1988 | McAnalley | 514/53 |
| 4,801,582 | 1/1989 | Hikino et al. | 514/54 |
| 4,851,224 | 7/1989 | McAnalley | 424/195.1 |
| 4,917,890 | 4/1990 | McAnalley | 424/195.1 |
| 4,957,907 | 9/1990 | McAnalley | 514/54 |
| 4,959,214 | 9/1990 | McAnalley | 424/195.1 |
| 4,966,892 | 10/1990 | McAnalley | 514/54 |
| 5,106,616 | 4/1992 | McAnalley et al. | 424/85.2 |
| 5,118,673 | 6/1992 | Carpenter et al. | 514/54 |
| 5,308,838 | 5/1994 | McAnalley et al. | 514/54 |
| 5,441,943 | 8/1995 | McAnalley et al. | 514/54 |
| 5,443,830 | 8/1995 | Moore et al. | 424/195.1 |

FOREIGN PATENT DOCUMENTS

| | | |
|---|---|---|
| WOA87 00052 | 1/1987 | WIPO . |
| WOA89 06539 | 7/1989 | WIPO . |

OTHER PUBLICATIONS

Paulsen et al. "Structural studies of the polysaccharide from Aloe plicatilis Miller", Carbohydrate Research, vol. 60: 345–351, 1978.

Gowda, "Structural studies of polysaccharides from Aloe saponaria and Aloe vanbalenii", Carbohydrate Research, vol. 83: 402–405, 1980.

Waller et al., "A chemical investigation of Aloe barbadensis Miller", Proc. Okla. Acad. Sci., vol. 58: 69–76, 1978.

Waller et al., "Current status of quality control of Aloe barbendensis extracts". Seifen, Oele, Fette, Wachse, vol. 119(5): 255–268, 1993.

Yagi et al., "Aloe Mannan, Polysaccharide, from Aloe Arobrescens var. Natalensis", Plants Medica, vol. 31: 17–20, 1977.

Womble et al., "Enhancement of Allo–Responiveness of Human Lymphocytes by Acemannan (Carrisyn)", Int. J. Immunopharmac., vol. 10(8): 967–974, 1988.

Solar et al., "Mise en evidence et etude des proprietes immunostimulantes d'un extrait isole et partiellement purifie a partir d'aloe vahombe", Arch. Inst. Pasteur Madagascar, vol. 47: 9–39, 1978.

Radjabi et al., "Structural studies of the glucomannan from Aloe vahombe", Carbohydrate Research, vol. 116: 166–170, 1983.

Database WPI, Section Ch, Week 8142, Derwent Publications Ltd., London, GB, AN 81–76459D, XP002011924 & JP,A,56 110 627 (Ajinomoto KK). Sep. 1, 1981.

Database WPI, Section Ch, Week 8142, Derwent Publications Ltd., London GB, AN 81–76458D, XP002011925 & JP,A,56 110 626 (Ajinomoto KK). Sep. 1, 1981.

Database WPI, Section Ch, Week 9506, Derwent Publications Ltd., London, GB, AN 95–040287, XP002011926 & JP,A,06 319 498 (Hirata Noen YG). Nov. 11, 1994.

CN,A,1 108 225 (Traditional Chinese Medicine R) 13 Sep. 13, 1995.

*Primary Examiner*—Howard C. Lee

[57] ABSTRACT

A bioactive Factor produced, separated and isolated from either an aloe vera leaf or a product derived and processed from an aloe leaf, such as raw aloe vera gel, freeze-dried aloe vera gel extract, bulk acetylated mannan and bulk pharmaceutical mannan, utilizing different sizing processes, their processes or preparations, and their uses. The process of sizing can be accomplished by centrifugation, filtration, ultrafiltration, chromatography, dialysis, selective precipitation, pH adjustment, irradiation, homogenizing, or a combination of such processes. Compounding or mixing two or more different bioactive Factors from aloe at various concentration ratios, each Factor with its own specific bioactivity or bioactivities, to obtain a new bioactive Factor having desired optimal additive or synergistic effects.

50 Claims, 19 Drawing Sheets

BIOACTIVE FACTORS OF ALOE VERA PLANTS

This application is a continuation of a co-pending application Ser. No. 08/532,060, filed on Sep. 22, 1995.

BACKGROUND

The present invention relates to bioactive Factor produced, isolated, and separated from either an aloe vera leaf or a product derived or processed from an aloe leaf, their preparations, and their uses. More specifically, the present invention relates to bioactive Factors produced, isolated and separated from an aloe vera leaf, aloe gel fillet, aloe raw gel, freeze-dried aloe vera gel extract, bulk acetylated mannan or bulk pharmaceutical mannan utilizing different sizing processes, their processes or preparations, and their uses.

Aloe is a tropical or subtropical plant characterized by lance-shaped leaves with jagged edges and sharp points. For centuries, this plant has been considered to have, and has been used for its, medicinal and therapeutic properties without any clear understanding or scientific analysis of the bases for such properties. Further, it is known that the biological activities of fresh aloe plant decay very rapidly.

Because of this lack of knowledge about the aloe plant and its characteristics, most methods employed for the processing of the plant result in end products which do not consistently achieve desired results. Further, aloe leaves contain anthraquinones in its yellow sap. The anthraquinone-containing yellow sap is known to have a laxative effect with a reputation as an extremely irritating cathartic. Traditional processes for the production of various aloe products typically involved crushing (pressure rollers), grinding (e.g., use of Thompson aloe leaf slitter), or pressing (TCX pressure extruder) of the entire leaf of the aloe plant to produce an aloe vera juice, followed by various steps of filtration and stabilization of the juice. The resulting mixture is then incorporated in, or mixed with, other solutions or agents to produce the products which could be, for example, a cosmetic, a health food drink, or a topical ointment. Unfortunately, because of improper processing procedures, many of these so-called aloe products contain no bioactive chemical substances or ingredients.

The principal disadvantage of such state of the art processes is the failure to recognize, and to take into account, that different fractions or components of the aloe leaf have different kinds of biological activities. These different fractions have characteristics that may not only be inconsistent with the intended use of the final product, but in many instances were deleterious to such use. Further, unless carefully controlled processes are used in processing the leaves of the aloe plant, the active chemical substances, or ingredients, of the leaves are destroyed during the process.

Aloe vera leaves contain a variety of chemical substances and components. Mixtures of active chemical substances of aloe leaves have been identified, isolated and stabilized as described in U.S. Pat. Nos. 4,735,935, 4,851,224, 4,917,890, 4,957,907, 4,959,214, and 4,966,892, each of these is incorporated herein by reference. One group of the active chemical substances has been referred to as aloe vera mucilaginous polysaccharides. Even the aloe vera mucilaginous polysaccharides are made up of a mixture of polysaccharides. The term "polysaccharides" has been used loosely to include both oligomers and polymers of carbohydrates. A group of such polysaccharides has been given the name acemannan. Acemannan is an ordered linear polymer of substantially acetylated mannose monomers.

The biological, or physiological, activities of aloe vera mucilaginous polysaccharides and their pharmaceutical applications have been the object of numerous research studies at a number of laboratories, including Carrington Laboratories. Uses of aloe products have been described in U.S. Pat. Nos. 5,106,616, 5,118,673, 5,308,838, 5,441,943, and 5,443,830, each assigned to Carrington Laboratories, Inc., the content of each of which is incorporated by reference herein. These studies have primarily focused on the activities of bioactive chemical substances of aloe vera as antiviral agents, antitumor agents, immunostimulants, immunomodulators, vaccine adjuvants, means of reducing opportunistic infections, means of controlling inflammation, and means of stimulating the wound healing processes.

Aloe vera mucilaginous polysaccharides have been shown in controlled studies to increase the rate of healing in animals. Aloe vera mucilaginous polysaccharides have also been shown to be an effective treatment for gastric ulcers in animal studies.

Acemannan, for example, has been shown in laboratory studies to increase up to 300% in 48 hours the replication of fibroblasts in tissue culture which are known to be responsible for healing burns, ulcers and other wounds of the skin and of the gastrointestinal lining.

Over a three year period, laboratory rats, the stomachs of which react similarly to that of humans, were tested. Acemannan was found to be equivalent to or superior to current medications used for the treatment of gastric ulcers. Most such products act to inhibit hydrochloric acid in the stomach. Acemannan works on a different principle and does not alter the natural flow of digestive acids.

In view of the known wide spectrum of biological activities possessed by leaves of aloe plant, and in view of the known complex mixtures of biologically active components and substances found in the leaves of aloe plant, it is desirable to isolate and separate different biologically active Factor from the leaves of the aloe plant. A need has arisen for sizing different Factors of bioactive chemical substances of aloe vera leaves.

SUMMARY

The problems discussed above have been solved in the present invention which provides for different bioactive Factors or fractions produced and isolated by sizing from either an aloe leaf or a product derived and processed from an aloe leaf, their manufacture and uses.

Broadly, one embodiment of the present invention is the process to obtain a bioactive Factor from either an aloe vera leaf or a derived or processed product of the aloe leaf.

Accordingly, an object of the present invention is to provide a bioactive Factor of aloe.

Another object of the present invention is to provide a mechanism for the separation of these bioactive Factors of aloe.

Yet another object of the present invention is to provide a process to obtain individual bioactive Factor of aloe.

Broadly, one method of producing a bioactive Factor from aloe contains the steps of:

(a) Filtering a starting material with a course filter, having a pore size ranging from about 400 $\mu$m to about 800 $\mu$m, to give a coarsely-filtered starting filtrate, the starting material being selected from the group consisting of a crushed aloe leaf, aloe gel fillet, aloe raw gel, and dried aloe vera gel extract;

(b) filtering the coarsely-filtered starting filtrate with a medium filter, having a pore size ranging from about 100 μm to about 400 μm to give a mediumly-filtered starting filtrate; and (c) sizing the mediumly-filtered starting filtrate with a method selected from pH adjustment, selective precipitation, centrifugation, ultracentrifugation, irradiation, further filtration, ultrafiltration, dialysis, homogenizing, and combination thereof.

Another general method to produce a bioactive Factor from aloe consists of the following steps:

(a) Filtering a starting material with a course filter having a pore size ranging from about 400 μm to about 800 μm, to give a coarsely-filtered starting filtrate, the starting material being selected from the group consisting of a crushed aloe leaf, aloe gel fillet, aloe raw gel, and dried aloe vera gel extract;

(b) filtering the coarsely-filtered starting filtrate with a medium filter, having a pore size ranging from about 100 μm to about 400 μm to give a mediumly-filtered starting filtrate; and (c) step-wise filtering the mediumly-filtered starting filtrate using filters having progressively smaller pore sizes starting from: a range of from about 25 μm to about 100 μm; to a range of from about 5 μm to about 25 μm; to a range of from about 0.1 to 5 μm; and to a range of from about 0.04 μm to about 0.1 μm.

Other objects, advantages and novel features of the present invention will become apparent from the following description of the invention.

In the FIGURES above, each box represents at least one bioactive Factor, similar to or different from the bioactive Factor from a different box. The drying process is preferably carried out by freeze-drying, and, after drying, a new bioactive Factor may be produced.

Figure 1:
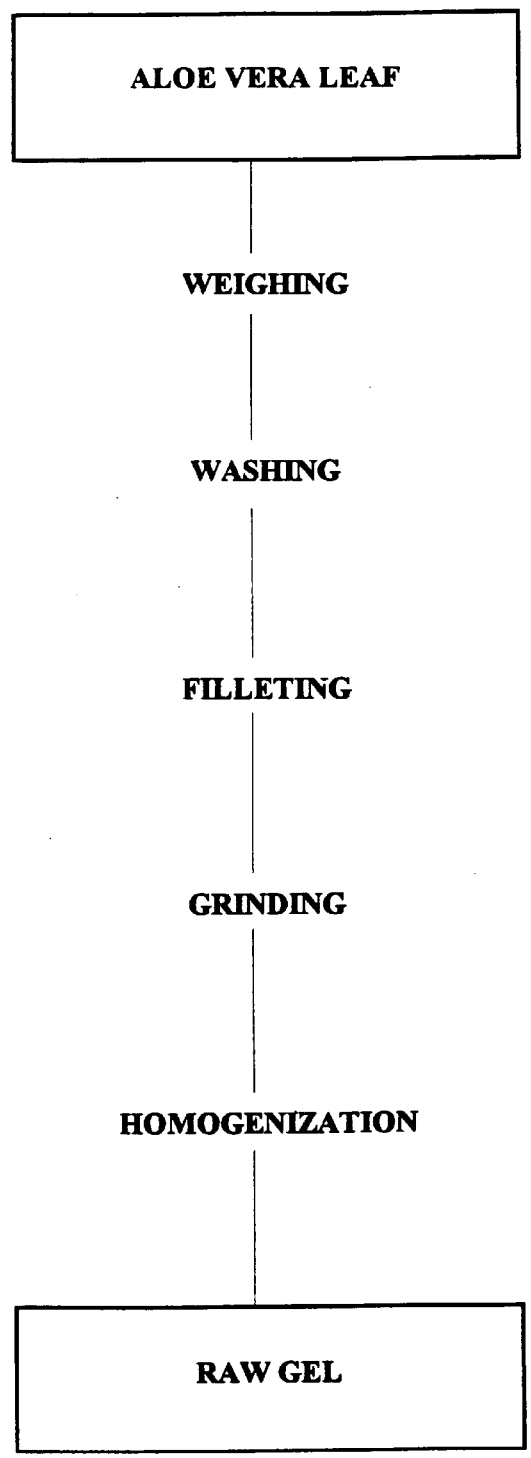
FIG. 1 shows a series of procedures and sizing steps involved in producing raw gel from an aloe vera leaf ("raw gel").
Figure 2:
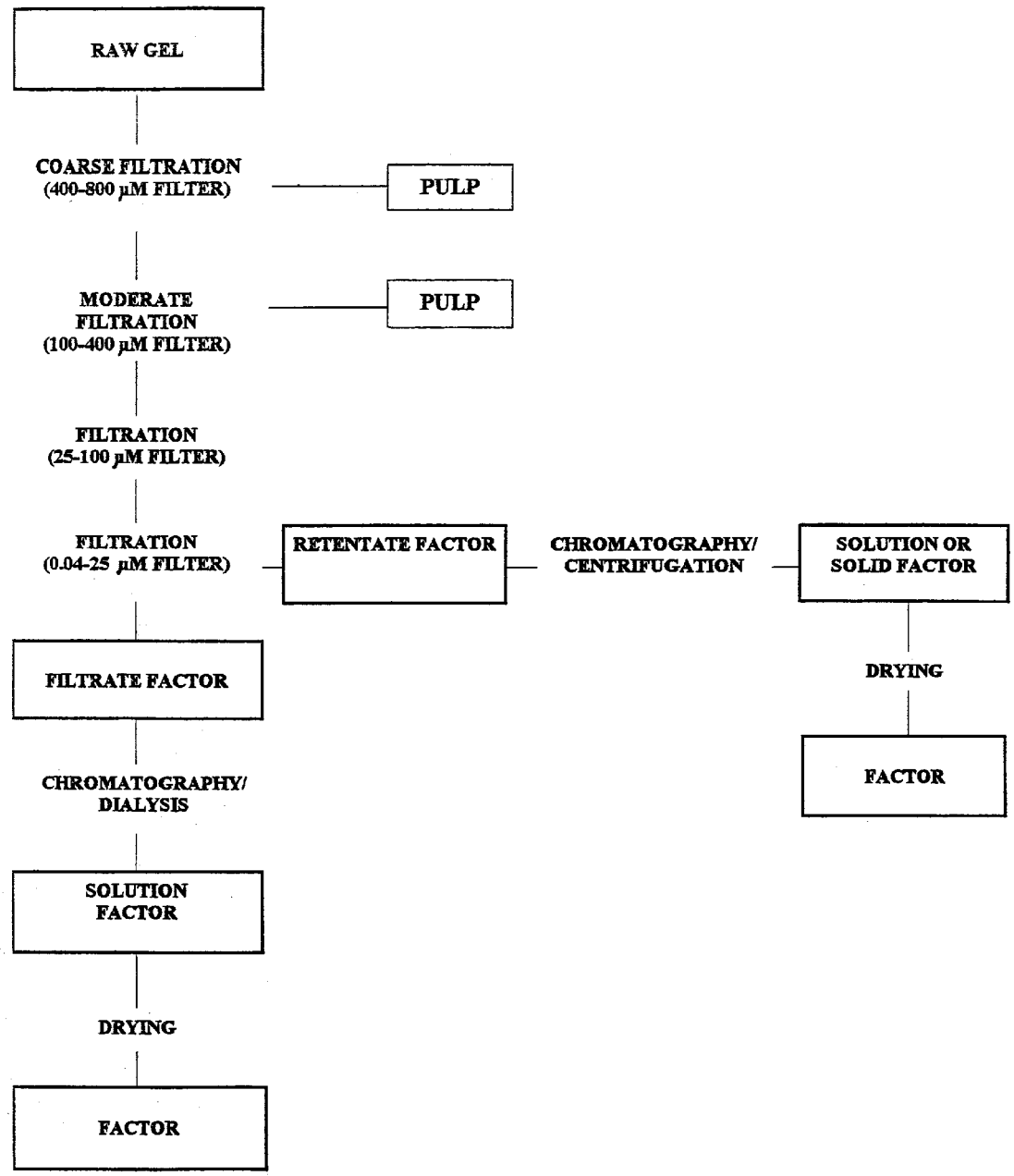
FIGS. 2–9 show subjecting raw gel from aloe vera to different procedures and sizing steps to produce different bioactive Factors.
Figure 3:
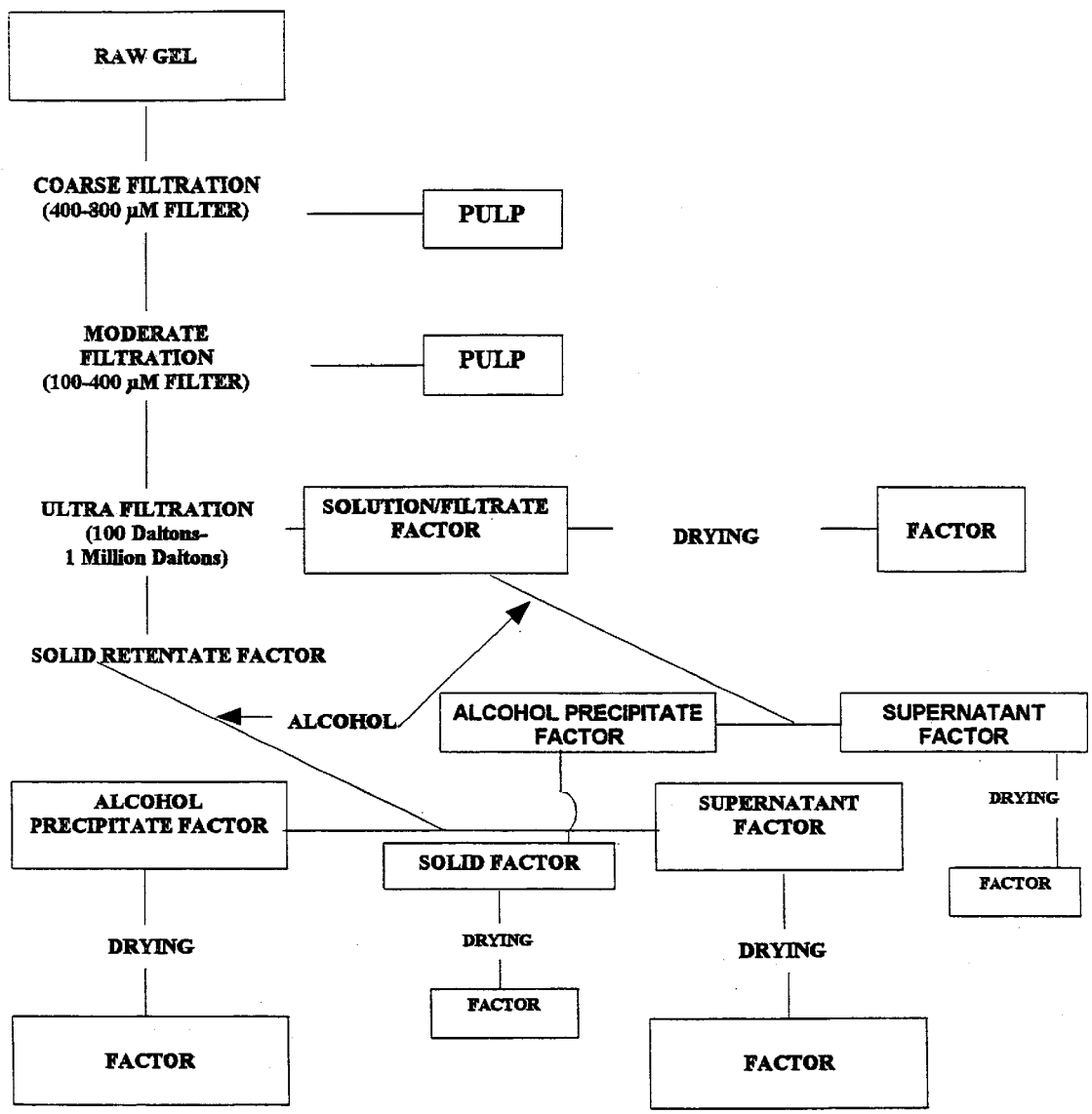
Figure 4:
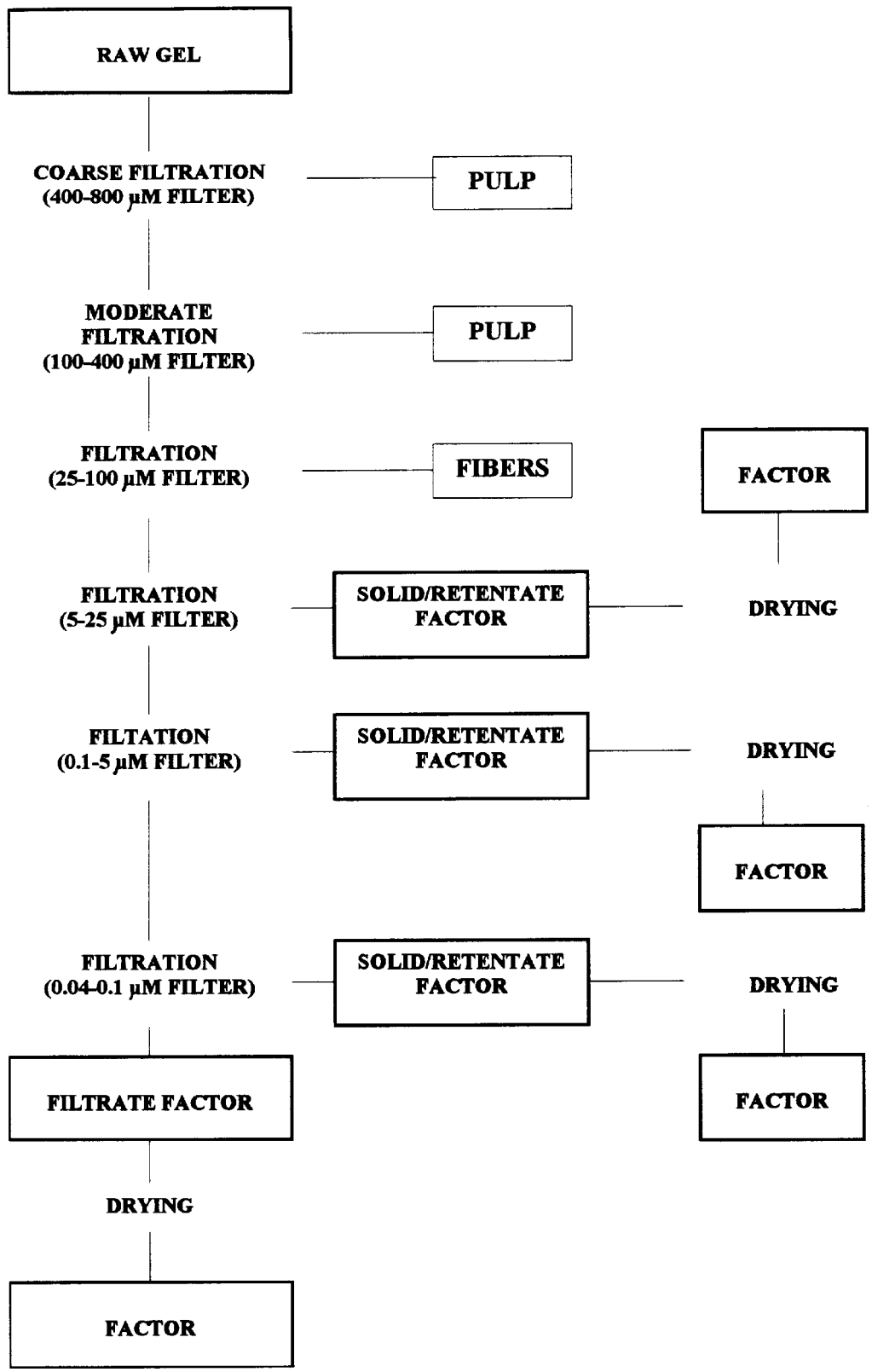
Figure 5:
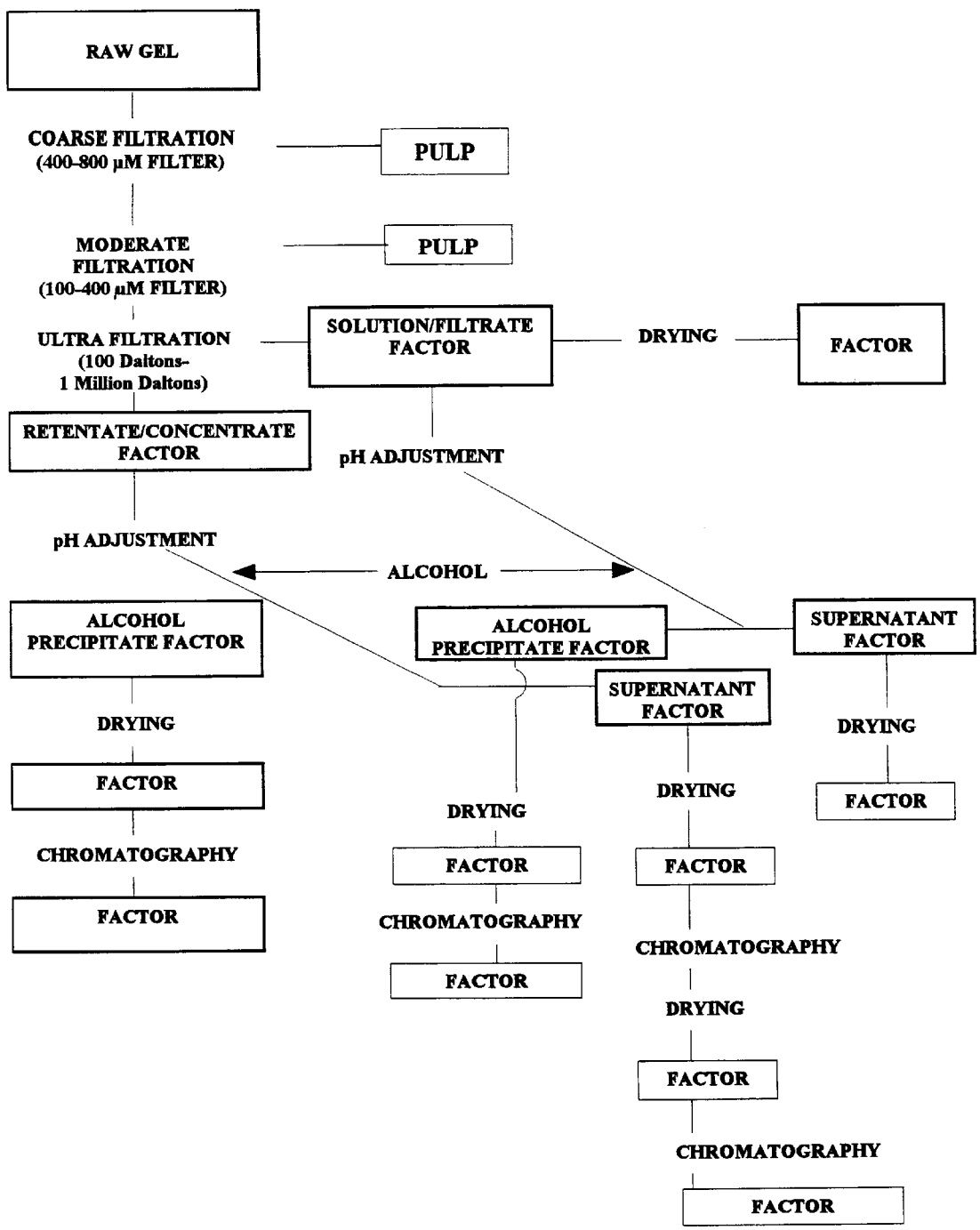
Figure 6:
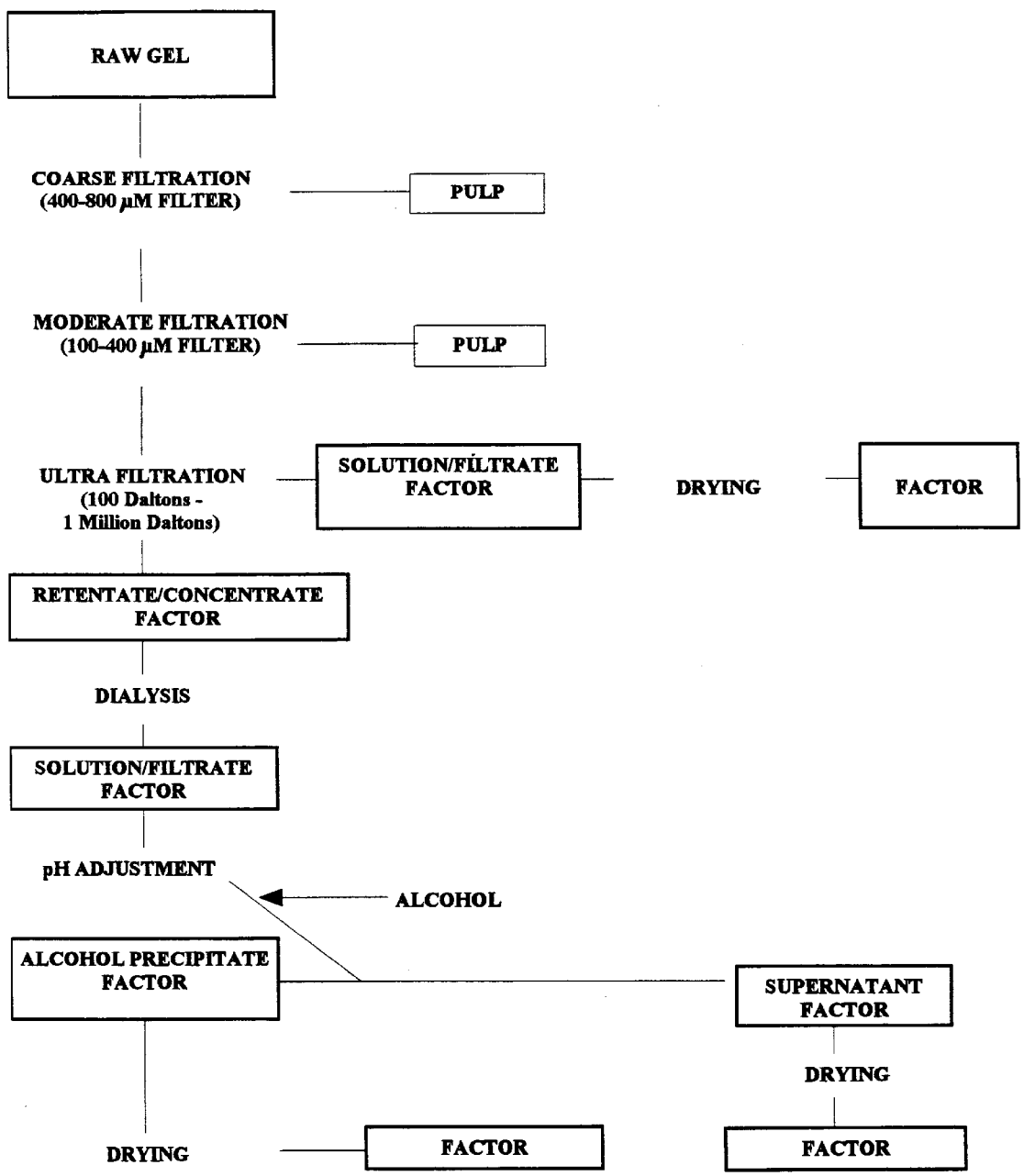
Figure 7:
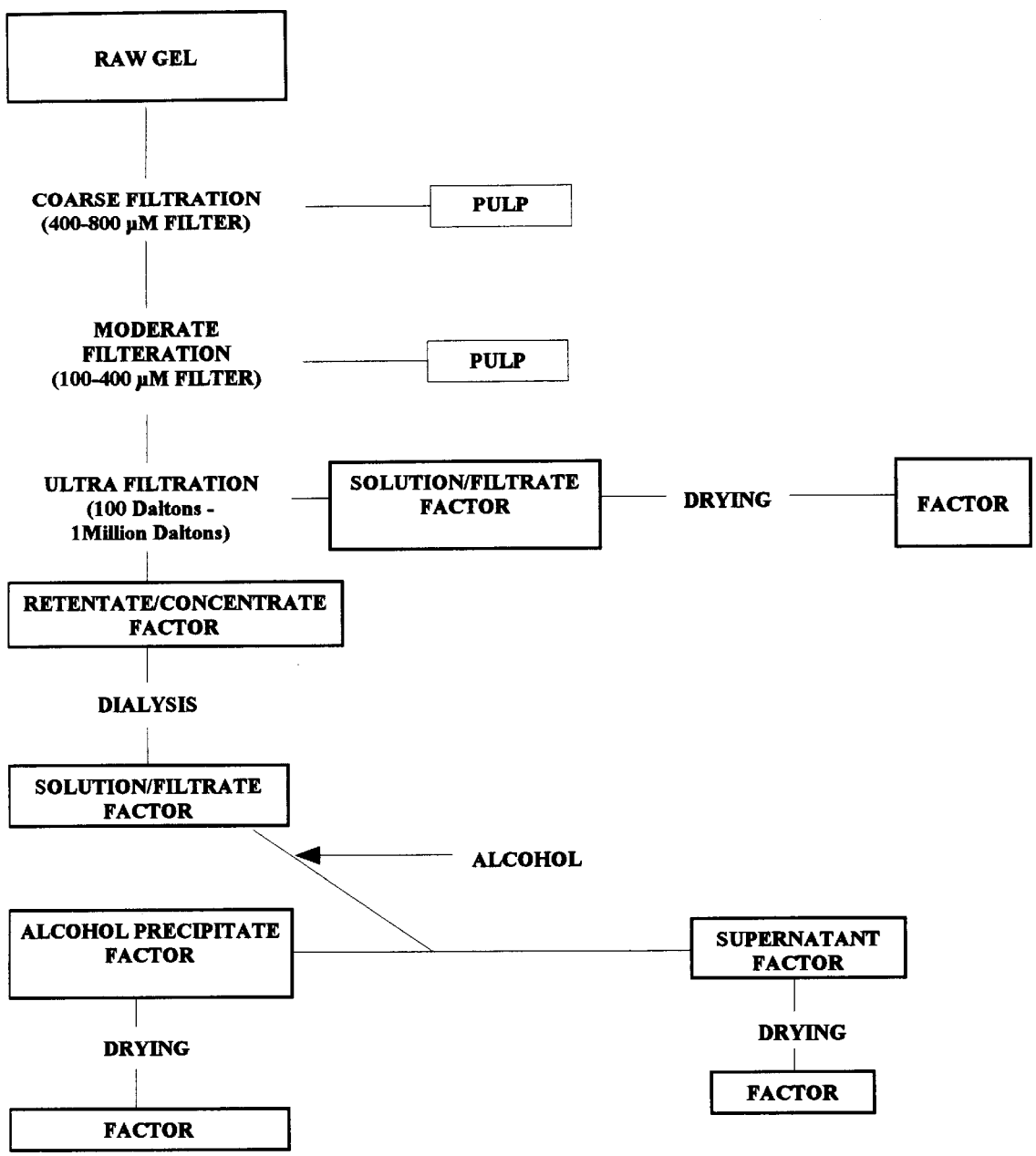
Figure 8:
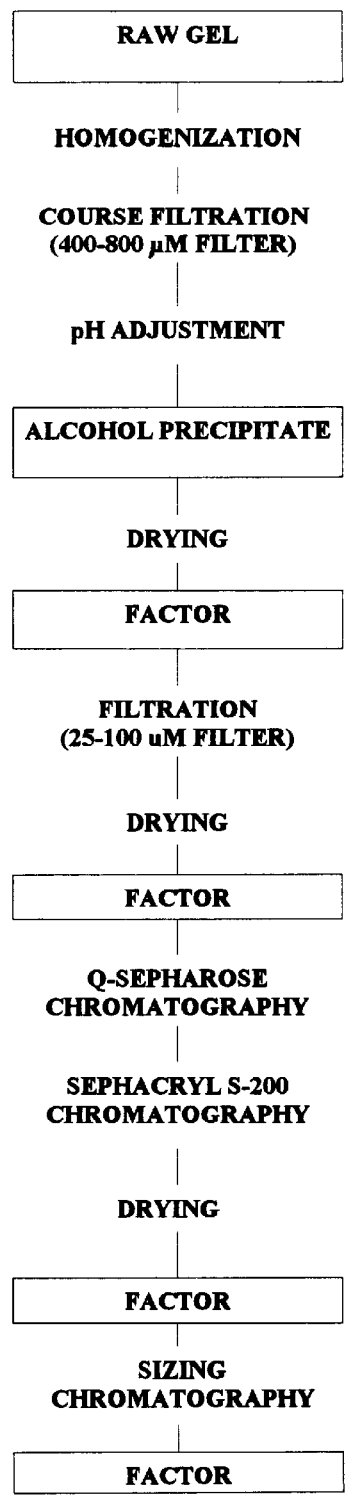
Figure 9:
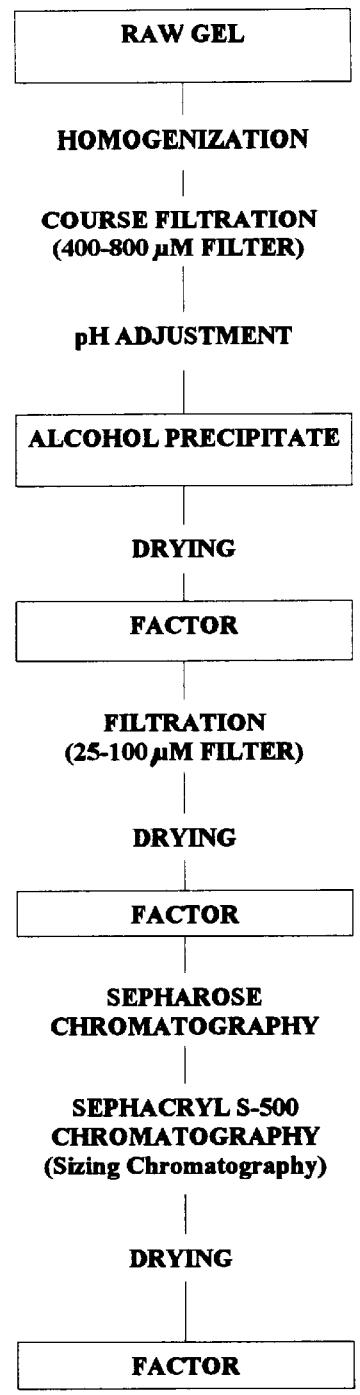
Figure 10:
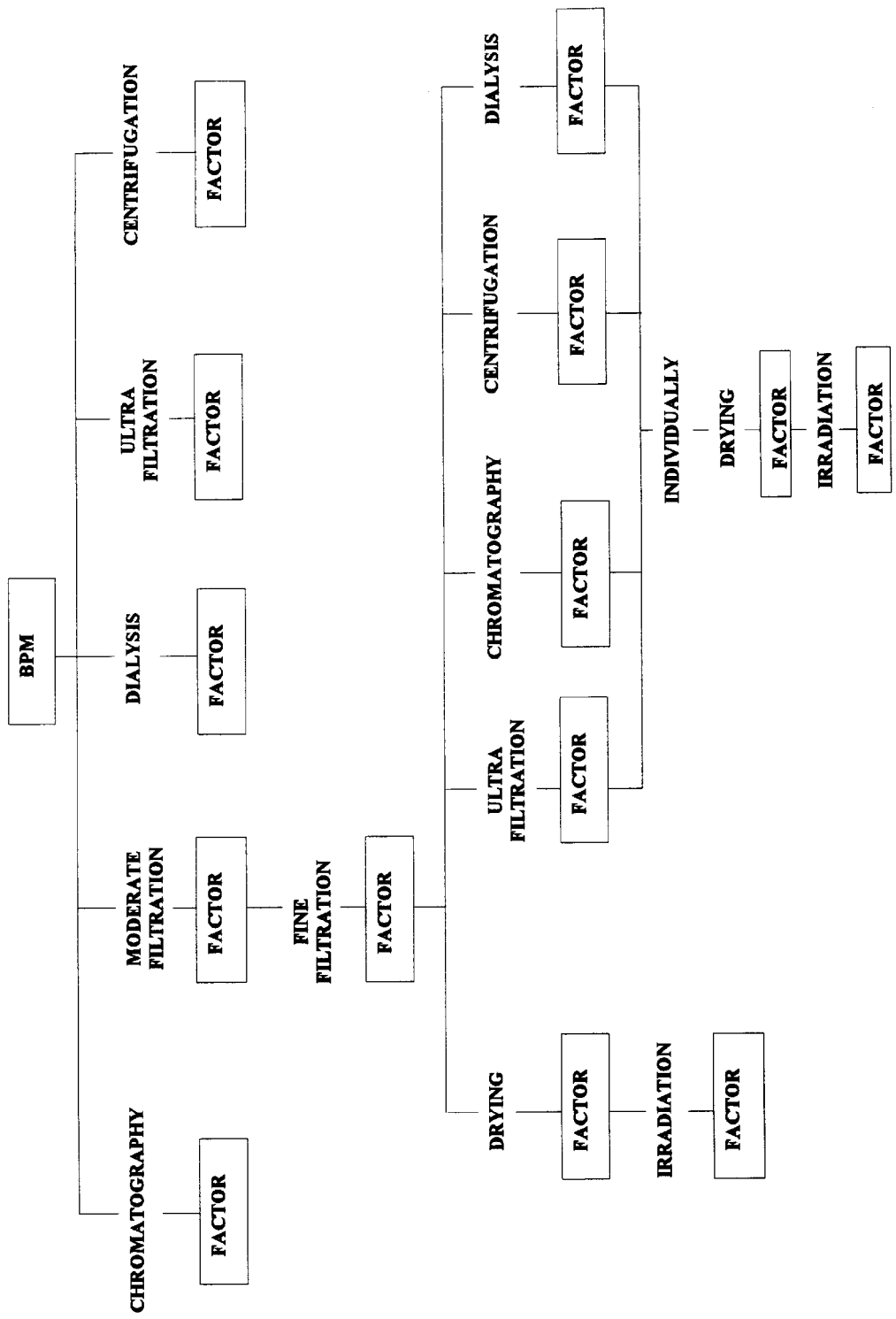
FIGS. 10 and 11 show different bioactive Factors produced, separated and isolated by different sizing steps using bulk pharmaceutical mannan ("BPM") as the starting material.
Figure 11:
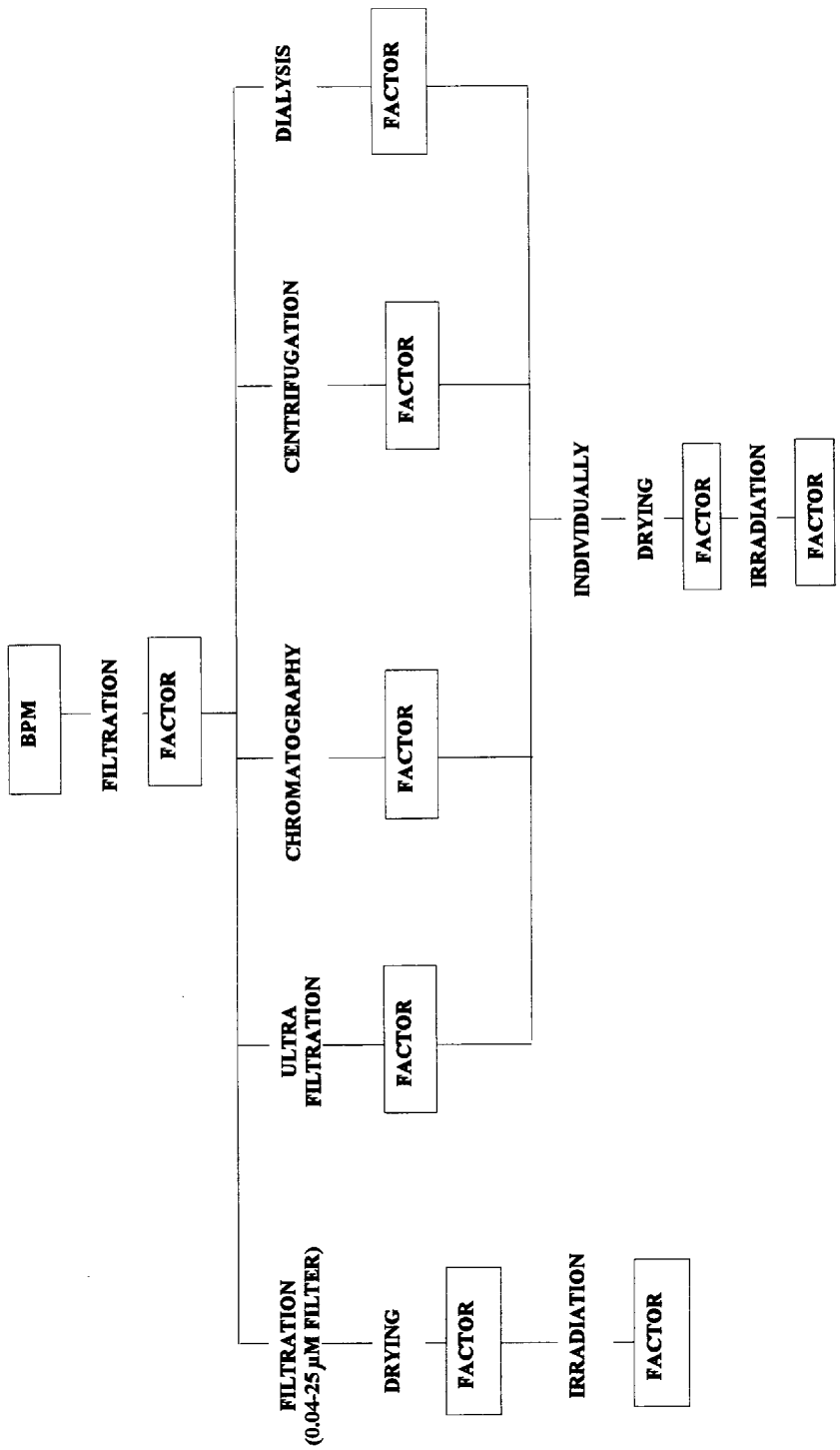
Figure 12:
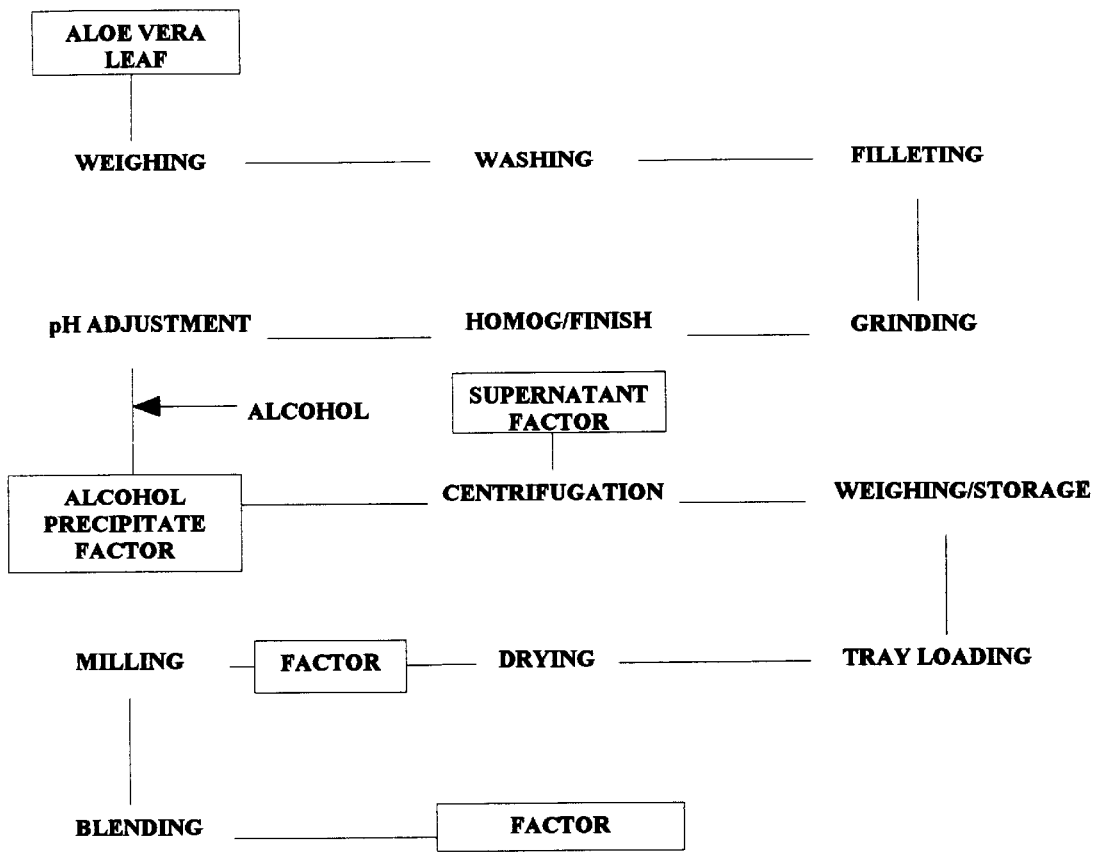
FIG. 12 illustrates yet another series of procedures and sizing steps in producing different bioactive Factors from an aloe vera leaf.
Figure 13:
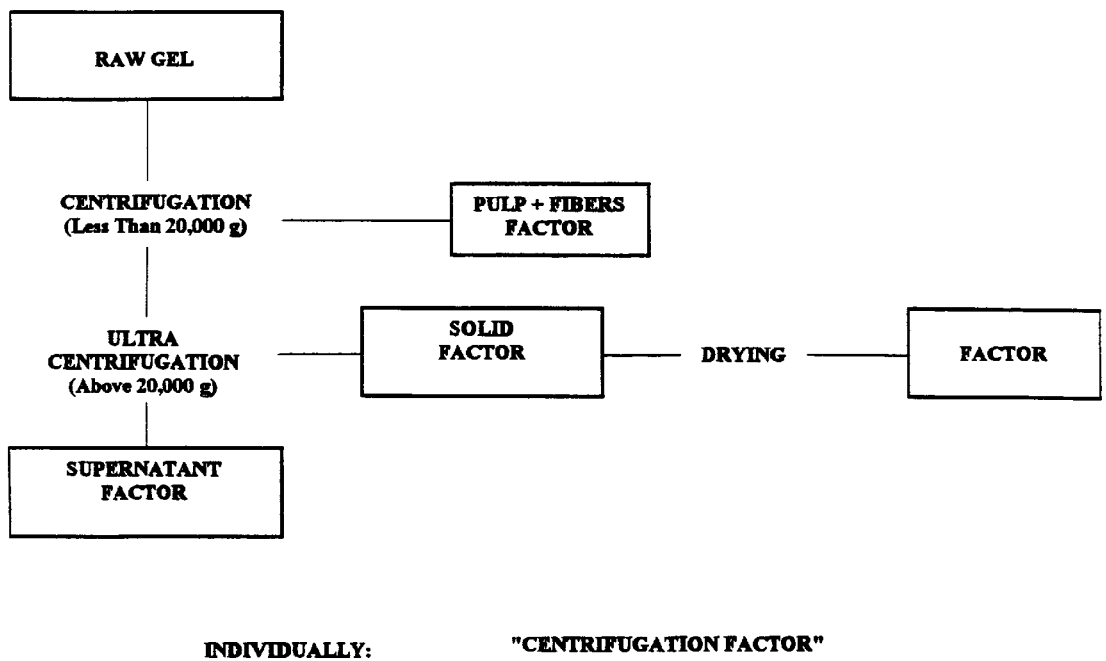
FIG. 13 shows producing different bioactive Factors from raw gel utilizing different procedures and centrifugation sizing steps. Each Factor so produced and obtained is loosely termed "Centrifugation Factor" for FIGS. 14–16.
Figure 14:
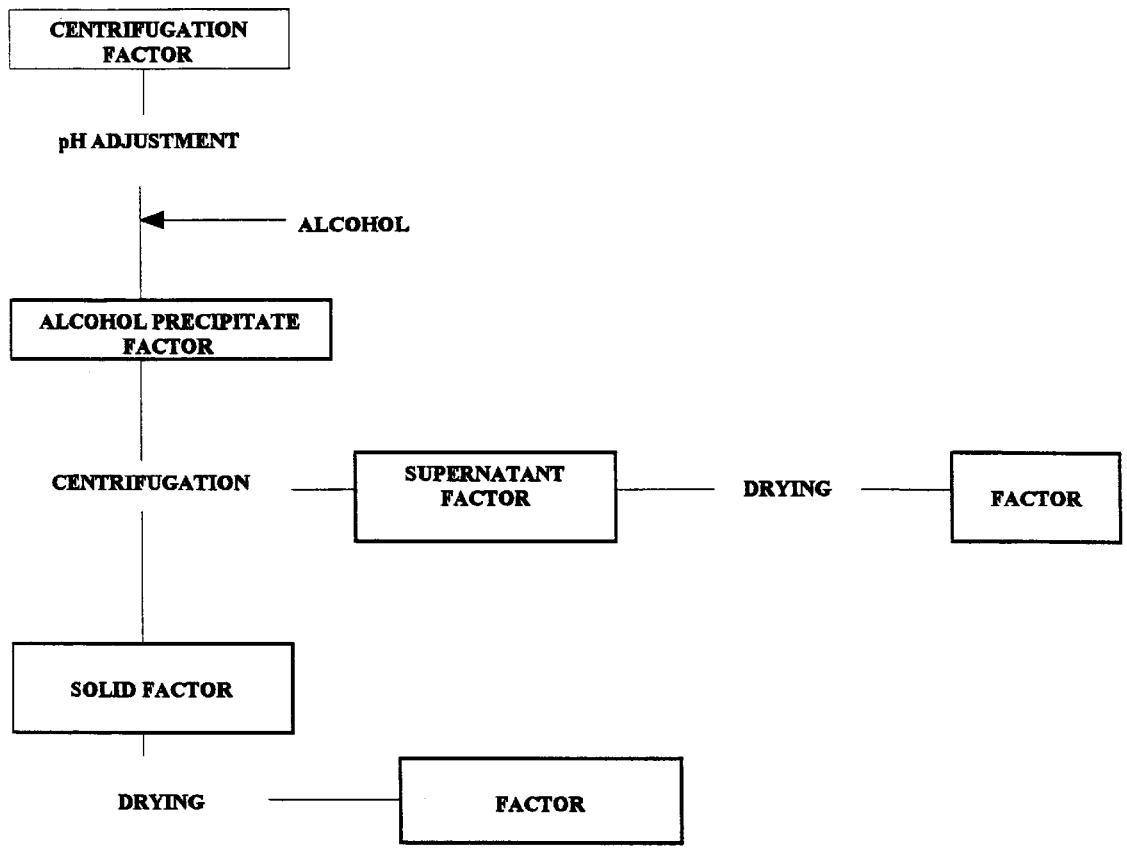
FIGS. 14–16 show subjecting any one of the bioactive Factors obtained from FIG. 13, "the Centrifugation Factor," to different procedures and sizing steps to produce different bioactive Factors.
Figure 15:
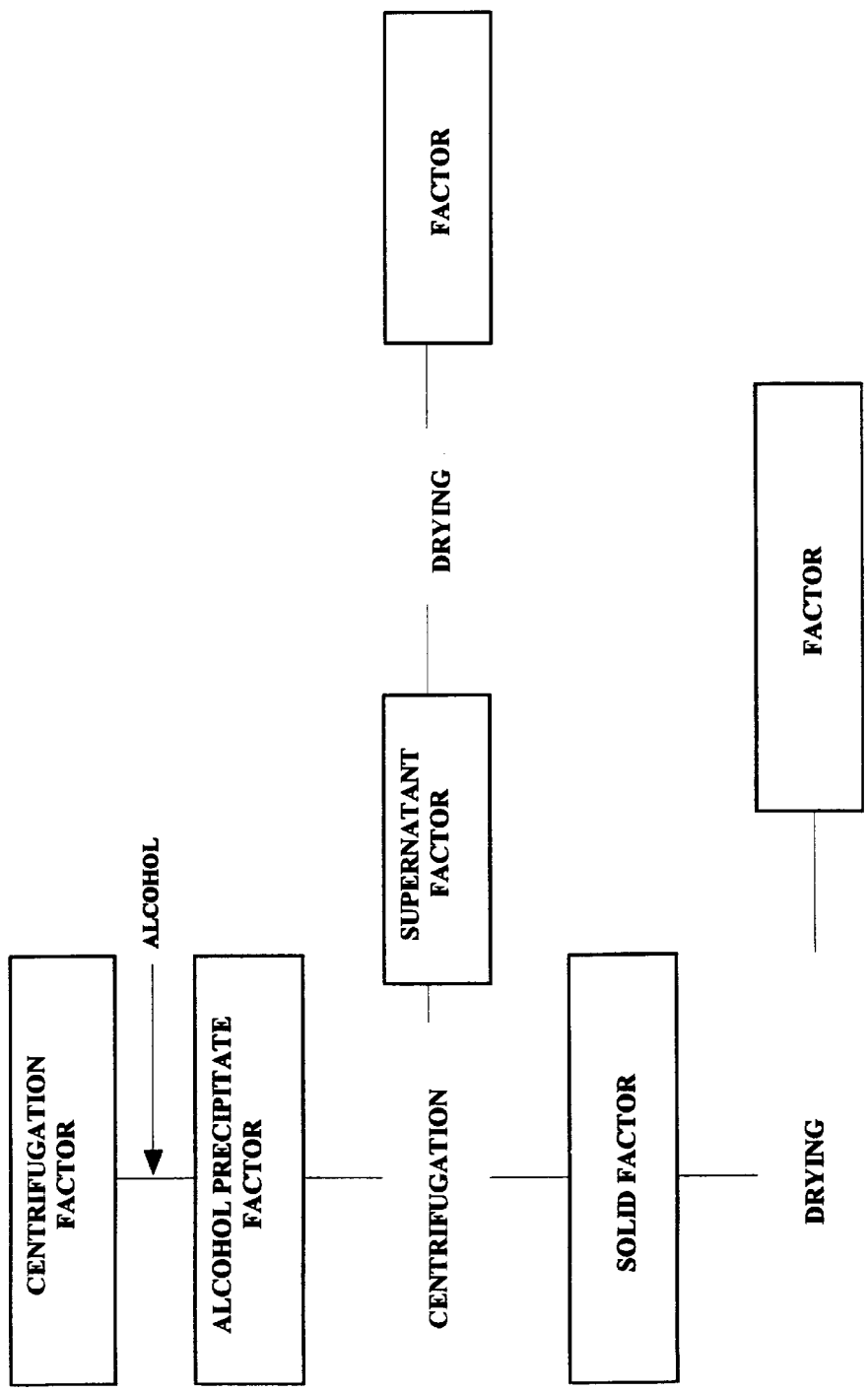
Figure 16:
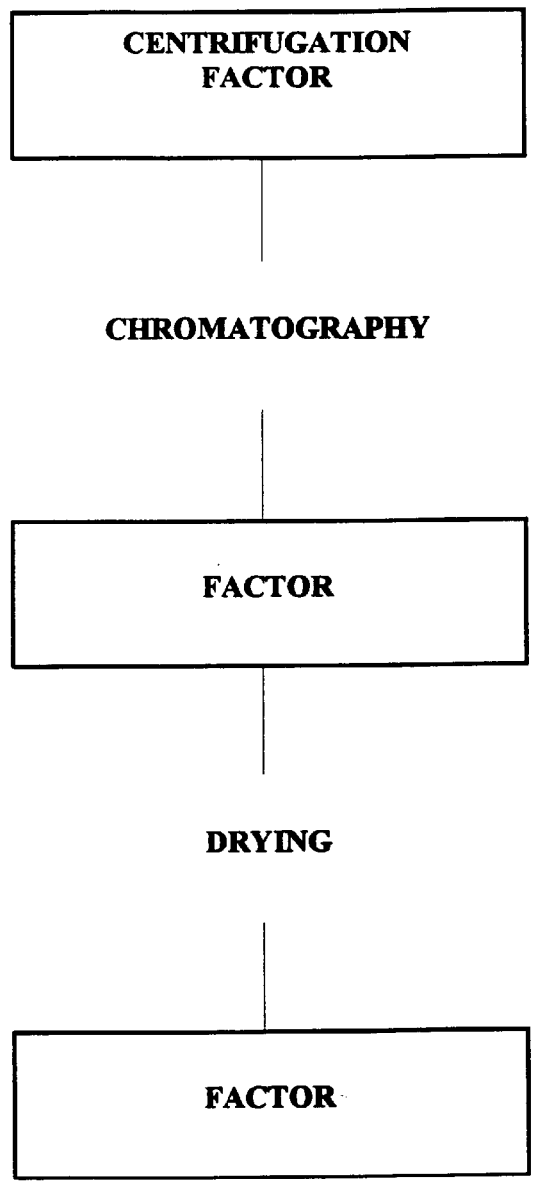
Figure 17:
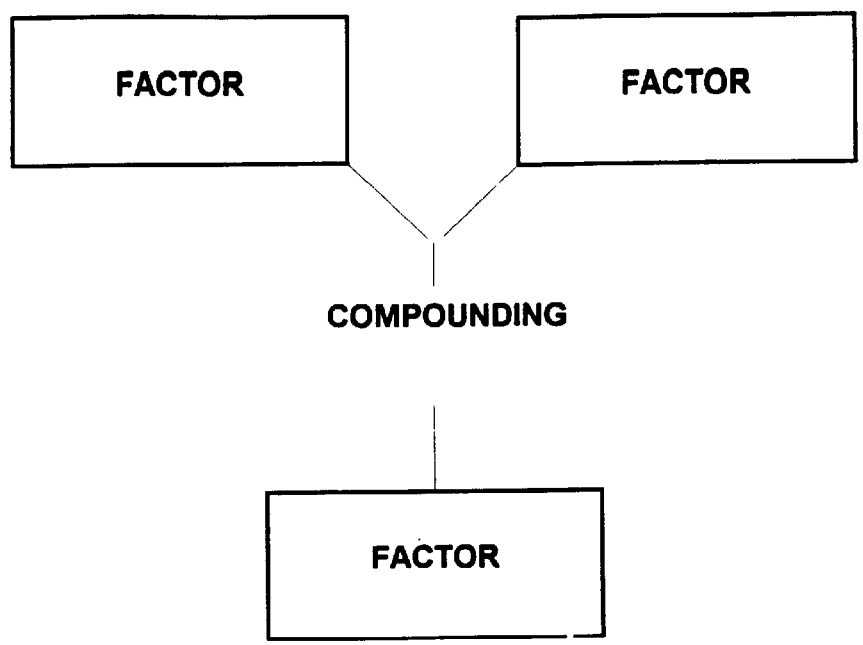
FIG. 17 shows compounding two or more different bioactive Factors to produce a different bioactive Factor.
Figure 18:
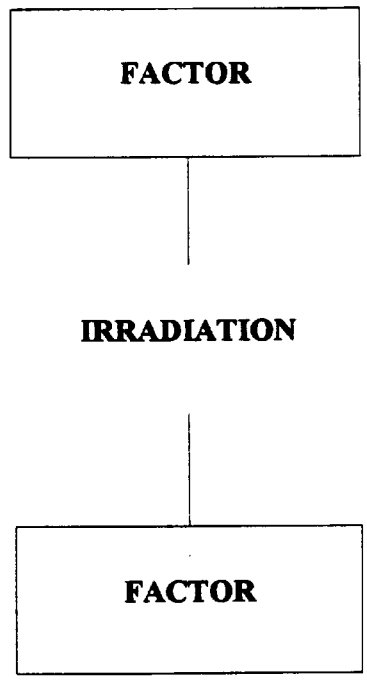
FIG. 18 shows irradiating bioactive Factor to produce a different bioactive Factor.
Figure 19:
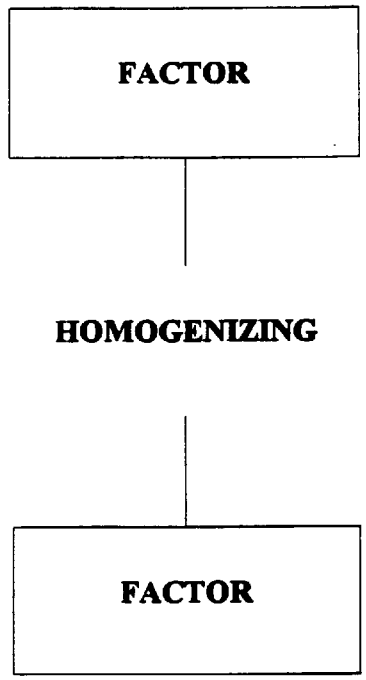
FIG. 19 shows homogenizing bioactive Factor to produce a different bioactive Factor.

In FIGS. 10 and 11, the "solution" Factor and the "solid" Factor (see below) are lumped together into one box. Each of the "solution" Factor and the "solid" Factor may then be subjected to further sizing steps. The word "individually" denotes that each of the Factors produced from different sizing steps can be subjected to further sizing processes to produce additional Factors.

DETAILED DESCRIPTION

The problems discussed above, inherent in the previously available different mixtures of bioactive chemical substances of aloe leaves have been solved in the embodiments of the present invention pertains, in one aspect, to production, separation, and isolation, such as by sizing, of a bioactive Factor from either aloe vera leaves or products derived or processed from aloe leaves.

As used herein, the term "bioactive" means "possessing biological activity," such as a pharmacological or a therapeutic activity. More specifically, the biological activity can be: Analgesic; antiviral; anti-inflammatory; antineoplastic; immune stimulating; immune modulating; adjuvant; or a combination thereof.

A substance has an "analgesic" activity if it can relief pain.

An "antiviral" activity is the activity of a substance that can interfere directly or indirectly with the replication of a virion or its infection and/or interaction with a host cell.

A substance has an "anti-inflammatory" activity if the substance can inhibit the inflammatory process of heat, redness, swelling, pain and loss of function as a result of tissue destructive processes and response.

An "antineoplastic" activity is the activity of a substance that can interfere with the cell cycle of tumor cells, that can prevent replication or repair of tumor cells, or that can increase programmed cell death or apoptosis, and/or effect the immunogenicity of tumor cells resulting in their destruction.

A substance has an "immune stimulating" activity if the substance can stimulate the immune system by either promoting cytokine release from macrophages, increase specific, or non-specific, phagocytosis, and/or stimulate directly or indirectly the components of the host defense system.

A substance has an "immune modulating" activity if the substance can interact with the immune system to either up-regulate (enhance) or down-regulate (lessen) the immune response.

A substance has an "adjuvant" activity if the substance can enhance, non-specifically, the immune response to an antigen. A substance is also known to have an "adjuvant" activity if the substance, when added, can assist a drug in a formulation to hasten or increase the action of the principal ingredient of the drug.

The word "Factor" is used to denote one or more chemical substances, or mixtures of different chemical substances, which chemical substances or mixtures thereof possess biological activity or activities. Such chemical substances could include a moiety such as an organic acid, protein, amino acid, carbohydrate, peptide, glycoprotein, sterol, other organic/inorganic substances, and mixtures thereof.

The word "sizing" as used herein means sorting/separating, grading and classifying according to density, solubility, particle size, molecular size, molecular weight, or a combination of the above. The process of sizing can be accomplished by centrifugation, filtration, ultrafiltration, chromatography, dialysis, selective precipitation, pH adjustment, irradiation, homogenizing, or a combination of such processes.

"Compounding" means mixing one Factor with at least one other dissimilar Factor at various concentration ratios to obtain a new Factor possessing a desired optimal additive or synergistic effect or effects.

Aloe gel fillet that is substantially anthraquinone-free can be produced by the following steps from a leaf of an aloe plant:

1. Washing the aloe leaf in a bactericidal solution to remove substantially all surface dirt and bacteria;
2. removing at least a first end portion from the washed leaf;
3. draining, preserving and collecting anthraquinone rich sap from the cut and washed leaf; and
4. removing rind from the leaf to produce a substantially anthraquinone-free gel fillet.

Aloe raw gel, "raw gel," or "aloe juice" that is substantially anthraquinone-free having solubilized and suspended matter can be obtained by grinding and homogenizing the substantially anthraquinone-free aloe gel fillet.

Freeze-dried aloe vera gel extract containing active chemical substance(s) or bioactive Factor from an aloe leaf can be produced by the following steps:

1. Obtaining aloe raw gel, "raw gel," or "aloe juice" having solubilized and suspended matter;
2. adding a water soluble, lower aliphatic polar solvent, such as ethanol, to the aloe juice to precipitate active chemical substance(s) and thereby forming a heterogeneous solution/suspension;
3. removing the water soluble, lower aliphatic polar solvent and the solubilized matter from the heterogeneous solution to isolate the precipitated active chemical substance(s); and
4. drying, preferably freeze-drying, the precipitated active chemical substance(s).

Another form of freeze-dried aloe vera gel extract containing active chemical substance(s) or bioactive Factor(s) from an aloe leaf can be produced by the following steps:

1. Obtaining aloe raw gel, "raw gel," or "aloe juice" having solubilized and suspended matter;
2. adjusting the pH of the aloe juice to from about 3 to about 3.5;
3. adding a water soluble, lower aliphatic polar solvent, such as ethanol, to the aloe juice to precipitate active chemical substance(s) and thereby forming a heterogeneous solution/suspension;
4. removing the water soluble, lower aliphatic polar solvent and the solubilized matter from the heterogeneous solution to isolate the precipitated active chemical substance(s); and
5. drying, preferably freeze-drying, the precipitated active chemical substance(s).

Generally, "bulk pharmaceutical mannan" ("BPM") may be prepared from aloe leaves as follows:

1. Aloe leaves are washed, sliced open and filleted to remove the leaf rind. The clean (substantially anthraquinones free) inner gel is retained while the green rind is discarded.
2. The filleted material is homogenized (creparo) and extensively filtered with a Finisher Model 75 (FMC, Chicago, Ill.), to remove most of the pulp.
3. The clear viscous gel is acidified to a pH of approximately 3.2 with dilute HCl.
4. The acidified gel is then extracted with four volumes of 95% ethanol at ambient temperature. Floating material is removed, then the alcohol/water mixture is siphoned off while the solid precipitate is collected by centrifugation. Most alcohol/water soluble substances such as organic acids, oligosaccharides, monosaccharides, anthraquinones and inorganic salts are eliminated by the alcohol extraction process.
5. The solid aloe vera extract is then washed with fresh alcohol, centrifuged, freeze dried, and ground to a white powder. The product at this stage still contains some moisture, protein, monosaccharides, oligosaccharides, organic/inorganic salts and other substances. The product can be stored as a source of BPM. The product is stable at room temperature in the freeze-dried form for several years if protected from additional moisture. The detailed procedures for producing substantially anthraquinone-free aloe gel, for producing substantially anthraquinone-free aloe juice, for extracting active chemical substance(s) from an aloe leave, for preparing BPM and for extracting from an aloe leave substantially non-degradable lyophilized ordered linear polymer of mannoses have been described in Carrington's U.S. Pat. Nos. 4,735,935, 4,851,224, 4,917,890, 4,957,907, 4,959,214, and 4,966,892, the entire content of each of which is incorporated by reference. The uses of aloe products have been described in Carrington's U.S. Pat. Nos. 5,106,616, 5,118,673, 5,308,838, 5,409,703, 5,441,943, and 5,443,830, the entire content of each of which is hereby incorporated by reference.

Filtered and irradiated bulk pharmaceutical mannan ("FBA"), another bioactive Factor, can be prepared and produced by filtering the BPM (using a filter having a pore size of about 25 $\mu$m) followed by gamma irradiation (about 2.5 MRad).

As shown in FIGS. 1–19, bioactive Factors can be produced and separated from either an aloe vera leaf or products derived and processed from the aloe vera leaf. Illustrative examples of the general ways to produce bioactive Factors by different sizing methods and by combinations of different sizing methods are given in FIGS. 1–19. The general procedures and general sizing methods found in FIGS. 1–19 are described below.

1. Weighing

Aloe vera leaves are weighed in baskets in a cart. Tare weight is measured for each cart.

2. Washing

Aloe vera leaves are soaked in a tank filled with potable water where they are washed. Two leaves per basket are sampled for a total of 32 per cart. Washed leaves are placed in the feeding flume (having chlorinated water with an initial 200 ppm chlorine concentration) or in clean baskets according to space availability. Leaves are fed to the processing lines in First-in-first-out ("FIFO") mode.

3. Filleting

Washed leaves are fed to the leaf-lines through a conveyor and rinsed with potable water immediately before being processed. Filleting consists of several consecutive steps: Base and tip removal; thorn removal; elimination of upper skin; and fillet extraction.

4. Grinding

Fillets are collected in a hopper and ground, producing the ground gel. The raw gel is processed in portions of 150–650 L/tank.

5. Homogenization

Ground gel is homogenized by passing it through a finely divided wire mesh, under pressure, to give raw gel.

Finishing (Coarse Filtration Using A Coarse Filter ):
Homogenized raw gel is "finished" (pulp removal by coarse filtration using a coarse filter such as a metal mesh of about 400–800 μm). The retentate, in this case the pulp, removed from the gel is weighed and usually discarded.

6. pH Adjustment

The pH of the gel is acidified (with 6N HCl) to pH 3.18–3.22 with constant mechanical agitation to maintain a uniform pH. The pH of the gel can be also made basic (with dilute NaOH).

7. Selective Precipitation

The gel is selectively precipitated in a water soluble, lower aliphatic polar solvent, such as 95% ethanol, using a 1:4.25 of gel:ethanol ratio. Addition and agitation speeds are regulated such that strands of precipitate are formed.

8. Centrifugation

Precipitation mix is centrifuged to isolate the solid product or cake. The effluent or supernatant, a mixture of ethanol and gel, is pumped out of the production area to be redistilled. Unless otherwise stated, centrifugation is normally carried out at below about 20,000 g for a period of greater than about 10 minutes and up to about 48 hours or longer. Preferably, the time period of centrifugation is about 30 minutes to about 3 hours.

9. Weighing/Storage

Centrifugation cake is weighed and stored temporarily in a freezer set at −10° C. Product is held in cold storage until approved for further manufacture.

10. Tray loading

Approved cake is loaded on lyophilization trays.

11. Drying

Drying is preferably accomplished by freeze-drying or lyophilizing. Trayed product is freeze-dried in the lyophilizer. Lyophilized product is double packed in High Density Polyethylene ("HDPE") labeled bags and weighed.

12. Milling

Lyophilized product is milled, double packed, labeled and weighed.

13. Blending

Ground product is blended. The product is double packed and labeled.

14. Storage and Exportation

The final product is sent to the warehouse where it is stored until exported.

15. Moderate or Medium Filtration (Filtration Using A Medium Filter)

The filtrate or gel, such as coarsely filtered gel, can be filtered by means of a medium filter having a pore size ranging from about 100 to about 400 μm filter. Filtration pressure is to be regulated between 2 and 50 psi. Pulp collected here, the retentate, is usually discarded and filtered gel is further processed.

Fine Filtration (Filtration Using A Fine Filter)

File filtration is usually accomplished by using a fine filter having a pore size ranging from about 0.04 to about 100 μm.

16. Ultrafiltration/Concentration

The moderately filtered gel or other filtrate or gel is ultrafiltered using a tangential flow ultrafiltration system (other systems such as tubular, plane filter, etc, can also be used) using a Polyvinyldinefluoride ("PVDF") hydrophobic membrane. Other usable membranes include polysulfone, cellulose, durapore, regenerated cellulose, synthetic plastic and inorganic ceramic materials. The substance that passes through the membrane will be collected and aloe vera bioactive Factor will be isolated from it. The substance that is concentrated containing high molecular weight product as another aloe vera bioactive Factor. Broadly, ultrafiltration is a molecular separation, separating a product or a Factor having a range of from about 100 to about 300,000 or even 1 million Daltons of molecular weight. The 1 million Daltons molecular weight product can normally be separated and isolated by a filter having a pore size of about 0.1 μm.

17. Ultracentrifugation

The supernatant suspension, (either the gel or a solution or suspension of another aloe vera bioactive Factor) is subject to centrifugation at, for example, about 20,000 to about 150,000 g. This process will yield a pellet called "microparticulate Factor" and a supernatant liquid called "supernatant Factor." The ultracentrifugation is normally carried out at above about 20,000 g for a period of greater than about 10 minutes and up to about 48 hours or longer. Preferably, the time period of ultracentrifugation is about 30 minutes to about 3 hours.

18. Low Speed Centrifugation

The suspension, (either the gel or a solution or suspension of another aloe vera bioactive Factor) is subject to a low speed centrifugation at from about 180 g to about 5000 g. This will yield a pellet which is discarded as it is mainly composed of cellular fibers. The supernatant/suspension is used for further manufacture.

19. Dialysis

A method by which large molecules and small molecules in solution are separated by selective diffusion through a semipermeable membrane. The filtered gel is dialyzed using a Millipore tangential flow dialysis system (other systems such as open tubular, plane filter, helicoidal rotating, etc., can also be used) using a Polyvinyldinefluoride ("PVDF") hydrophobic membrane. Other usable membranes include polysulfone, cellulose, durapore, regenerated cellulose, synthetic plastic and inorganic ceramic materials. Deionized ("DI") water is added to the recirculation tank at the same rate that the filtrate exits the system such that the total volume remains constant. The washing volume of DI water is to be from 4 to 20 times the initial volume. The substance that gets concentrated contains the higher molecular weight product.

20. Anion Exchange Chromatography

The filtered starting material is subjected to a separation using anion exchange chromatography using Q-Sepharose as the stationary phase. Other anion exchangers that could be used include Amberlite from Rohm and Haas, DEAE—Diethyl Aminoethyl—Sepharose, etc. The mobile phase is DI water. A buffer such as an acetate buffer of pH 4.5±2 could also be used. The solution or suspension of the starting material is fed into the column. The product is collected from the moment a signal is recorded in the u.v. (220–260 nm) detector of 0.002–0.02 Absorbance Units Full Scale ("AUFS") until the signal goes back to the baseline (±20%). The column is then washed with 3 M Sodium Chloride and 1 M Sodium Hydroxide followed by DI water to neutral pH.

21. Size Exclusion Chromatography

The solution or suspension of the starting material is pumped into the sizing column, such as Sephacryl S-200 or Sephacryl S-500, the collection of the material is started when the first u.v. signal is recorded (220–260 nm) with the detector at 0.002–0.02 AUFS. As many bioactive Factors of decreasing molecular weight as needed can be collected with this method and the range of molecular weight can be adjusted at will. Each of these bioactive Factors collected by size exclusion could be further processed by means of centrifugation, filtration, partition, adsorption, ion exchange, reverse phase, hydrophobic interaction or affinity chromatography and other sizing methods to yield a Factor consisting of single or combined chemical entities.

22. Step-Wise Filtration

Filtered starting material, (from step 15), can be filtered again using a series of filters of different pore sizes in order to produce and isolate different Factors present in Aloe. The first filter is a 25–100 μm filter, it removes fibers coming from the pulp. The filtrate is then filtered again through a 5–25 μm filter. The resulting solution or filtrate is collected. The solid collected on the filter can be recovered by backwashing the filter with DI water.

The filtrate from the previous filtration can then be filtered through a 1–5 μm filter, the resulting solution/filtrate collected and the solid collected on the 1–5 μm filter can be recovered by back-washing the filter with DI water. The filtrate from the previous filtration can then be filtered through a 0.1 to a 1.0 μm filter, the resulting solution collected and the solid collected on the 0.1–1.0 μm filter can be recovered by back-washing the filter with DI water. If needed, even finer core size filters, down to 0.04 or even lower μm filters, can be used to filter the resulting solution from above. Using different pore size filters in the filtration process will yield different "grade" of Factors.

The irradiation of a product is usually carried out by irradiating a dried product with gamma rays.

In certain sizing steps, "solid" Factor and "solution" Factor can be produced. For example, centrifugation will produce a supernatant Factor and a pellet Factor; and filtration will produce a filtrate Factor and a retentate Factor. Each of these Factors can be subjected to further sizing processes to produce additional Factors.

The pellet material from a centrifugation process or the retentate material from a filtration process is usually re-suspended or re-dissolved in a solvent before being subjected to other sizing processes.

In the sizing of an aloe product, the same sizing process or step can be utilized more than once in the production scheme. Thus, for example, a Factor obtained from a filtrate can be subjected to further filtration.

Various modifications of the disclosed processes to produce different bioactive Factors from aloe, as well as alternative modifications, variations and equivalents will become apparent to persons skilled in the art upon reading the above general description. The following examples are illustrative only and are not intended to limit the scope of the appended claims, which cover any such modifications, equivalents or variations.

EXAMPLE 1

PREPARATION OF BULK PHARMACEUTICAL MANNAN ("BPM")

Aloe leaves suitable for use were washed in 0.02% calcium hypochlorite. After rinsing with water, leaf tips and butts were removed, and leaves were inspected once again for damaged areas which were trimmed away.

Cleaned, trimmed leaves were filleted by hand or are fed by hand into the slitter, which separated the outer leaf rind from the leaf pulp. Fillets were funnelled into a grinder; rinds were collected for disposal. The ground aloe gel discharged from the grinder was collected in covered stainless steel tanks.

The tank containing the ground aloe gel was moved to an area where the gel was homogenized in a Crepaco homogenizer. The homogenized gel or "raw gel" was discharged into another stainless steel tank and transferred to the finisher area for filtration.

The raw gel was then pumped through the finisher, a horizontal screw-type extractor (FMC), to filter out the pulp which was discarded. One hundred gallons of filtered gel was pumped into a 100-gallon stainless steel tank.

The filtered gel was then adjusted with 6N hydrochloric acid to a pH of approximately 3.2.

The pH adjusted gel was "ethanol precipitated" by adding the gel to the alcohol at ambient temperature at a ratio of 1 part gel to 4 parts alcohol and mixed in a 550 gallon stainless steel tank until the flocculent precipitate formed.

Once the precipitate formed, the batch was mixed slowly while being transferred by a positive displacement pump to a continuous flow Sharples centrifuge for collection of the BPM which was then freeze-dried under reduced pressure of about 100 mTorr. Shelf temperature was set at 30° C.; the product was freeze-dried for approximately 24 hours or until all temperature probes reached 30° C.

EXAMPLE 2

PILOT SCALE SIZING OF BULK PHARMACEUTICAL MANNANS BY ULTRA-FILTRATION

Approximately 20 grams of BPM is dissolved and suspended in 20 liters of DI water by shaking overnight at 4° C. The solution/suspension is then concentrated at 4° C. on an Amicon DC-10L (Danvers, Mass.) using an Amicon H26P100-43 (100K cut-off) hollow fiber membrane cartridge until only 4 liters of retentate remains. Care was taken to maintain a head pressure below 25 psi. An additional 4 liters of DI water is then added and the remaining solution/suspension is concentrated to a volume of 4 liters. This fraction contains Factor greater than 100K Daltons and is subsequently lyophilized.

The filtrate (approximately 20 liters) is then concentrated using the same equipment with an Amicon H26P10-43 (10K cut-off) hollow fiber membrane cartridge at 4° C. until only 4 liters of retentate remain. An additional 4 liters of DI water is then added and the remaining solution is concentrated to a volume of 4 liters. This fraction contains Factor between 10K and 100K Daltons and is subsequently lyophilized.

The filtrate (approximately 20 liters) is then concentrated using the same equipment with an Amicon H53P3-20 (3K cut-off) hollow fiber membrane cartridge at 4° C. until only 4 liters of retentate remain. An additional 4 liters of DI water is then added and the remaining solution is concentrated to a volume of 4 liters. This fraction contains Factor between 3K and 10K Daltons and is subsequently lyophilized.

The filtrate (approximately 20 liters) containing Factor with molecular weights less than 3K Daltons is then lyophilized as described below.

All fractions are loaded into 12×24×2 inch stainless steel lyophilization trays, frozen to −45° C. and freeze-dried using a Virtis Unitop 800 with Freezemobile 24 (Gardener, N.Y.). After lyophilization, the factors were milled, and characterized.

EXAMPLE 3

PURIFICATION AND DEPYROGENATION OF FBA USING CHROMATOGRAPHY WITH SUBSEQUENT MOLECULAR SIZING (DFBA)

BPM that had been filtered (to 25 $\mu$m) and gamma irradiated (approximately 2.5 MRad) yielded filtered and irradiated BPM ("FBA") that was further purified and processed using chromatographic techniques.

FBA, lot 001FBC003, consisting of 11.0 grams, was solubilized with 2.2 liters of Water for Injection, USP (WFI) using a homomixer. The FBA solution/suspension was then loaded onto a Q-Sepharose Fast Flow (Pharmacia) column that had been previously equilibrated with 2.95% Sodium Chloride. All of the material was loaded on the column and eluted at a flow of 0.5 liters/min with WFI using UV absorbance at 214 nm. Fractions were collected until absorbance values reached baseline (+/−5% at 0.05% AUFS).

The fractions were then pooled, and loaded onto a Sephacryl S-200 (Pharmacia) column and desalted at 0.25 l/min using WFI. Product was collected when the UV signal started to increase at 214 nm and stopped when the signal reached baseline (+/−5% at 0.002 AUFS). The depyrogenation of FBA (DFBA, lot #021101) was lyophilized and characterized with endotoxin levels reduced from 23.4 to 0.9 eu/mL by Limulus Amebocyte Lysate ("LAL").

To further process and separate the product into different molecular size bioactive Factors, 3.5 grams of the product (DFBA, lot #021101), was solubilized in 700 mL of WFI loaded onto a Sephacryl S-500 HR column using WFI as eluent. Various molecular size Factor solutions were collected in 1 liter volume fractions with molecular weights decreasing with increasing elution volume. Fraction solutions were pooled, lyophilized and milled to produce four Factors with different average molecular weights ranging from 231K to 78K. The yields of the Factors is summarized as follows:

| Bioactive Factor | Yield (grams) | Average Molecular Wt. (Daltons) |
|---|---|---|
| 1 | 0.92 | 231K |
| 2 | 0.79 | 153K |
| 3 | 0.51 | 105K |
| 4 | 0.40 | 78K |

The remaining mass balance of 0.88 grams consisting of material with smaller average molecular weights was discarded, but could be collected if needed.

EXAMPLE 4

ANTIVIRAL EFFECTS OF DIFFERENT FACTORS OBTAINED BY CHROMATOGRAPHIC SEPARATION OF FBA

Several bioactive Factors were prepared using Chromatographic sizing of FBA. Factors 4, 5, 6, 7 and 8/9 were tested for antiviral effect using an enveloped RNA virus-Newcastle disease virus (NDV). NDV is a major pathogen in poultry. Viruses were propagated in 9-day-old chicken embryos, and viral infectivity was measured by $TCID_{50}$ in chicken embryo fibroblasts (CEFs).

To determine the antiviral effect of test samples, CEFs cultured were infected with serial dilutions of NDV stocks. After a one-hour absorption period, cells were washed and incubated in the presence of the test material at various concentrations. Cells then went through three cycles of freeze-thaw, and infectious titers in infected cell lysates were measured by $TCID_{50}$. A significant reduction in infectious titers was regarded as the positive antiviral effect.

Results:

The Factors tested had a varying degree of antiviral effect based on size. The DFBA had an antiviral effect with an inhibitory concentration equal to ±50 $\mu$g/mg, from which the other Factors were obtained by sizing chromatography. The other Factors had no antiviral effect except Factor 8/9. Factor 8/9 was as active as DFBA with an inhibitory concentration equal to ±50 $\mu$g/mg. Factor 8/9 had the lowest molecular weight.

ANTIVIRAL EFFECTS OF DIFFERENT FACTORS OBTAINED BY CHROMATOGRAPHIC SEPARATION OF FBA

| Factor(s) | Inhibitory Concentration ($\mu$g/ml) | Progeny Titer | Progeny Titer Based Antiviral effect |
|---|---|---|---|
| DFBA | ±50 | $10^{-1}$ | Pos |
| 4&5 | >200 | $10^{-5}$ | Neg |
| 6 | >200 | $10^{-5}$ | Neg |
| 7 | ±100 | $10^{-5}$ | Neg |
| 8&9 | ±50 | $10^{-1}$ | Pos |

EXAMPLE 5

ASSAYS USED TO DETERMINE BIOACTIVITY OF DIFFERENT BIOACTIVE FACTORS

A. PROTOCOL OF NITRIC OXIDE ("NO") ASSAY

Role of nitric oxide synthesis in macrophage antimicrobial activity has been reported by C. F. Nathan and J. B. Hibbs, Jr., in *Current Opinion in Immunology,* 3:65–70 (1991), incorporated by reference herein.

Macrophages are a population of widely distributed leukocytes. Macrophages are currently viewed as multipotential or multifaceted cells. They are phagocytic and constitutively express numerous receptors. The process of macrophage activation is complex and stimulus-dependent. Macrophage activation probably involves up-regulation of gene functions by endogenous or extracellular stimuli for effective antimicrobial immunity, i.e., antimicrobial immunity is dependent on macrophage activation. The most widely accepted model of macrophage activation suggests that it is a two-stage process involving both priming and activation. Activation can be delineated by analysis of the products of genes induced by activation.

Up-regulation of inducible nitric oxide synthase ("iNOS") has been shown to occur following activation. The product of iNOS is nitric oxide ("NO"). NO itself is a short-lived radical gas with a half life of 6–30 seconds. NO is derived from the oxidation of the terminal guanidine nitrogen atom of L-arginine by the NADPH-dependent enzyme iNOS. Once produced, NO reacts with molecular $O_2$ to form reactive nitrogen intermediates including $NO_2$, which subsequently reacts with water to produce nitrite or nitrate ions. Nitrite ions can be detected using a colorimetric assay and, therefore, used to quantitate macrophage activation.

A method for quantitating an oxidation, the preactive and the methods for quantitation of NO production are described herein.

Procedures:

1. Cells and Culture media:

RAW 264.7 cells, a mouse macrophage cell line, obtained from the American Type Culture Collection are cultured in Dulbecco's modified medium (GIBCO, endotoxin free) supplemented with 10% fetal bovine serum, and 1% penicillin/streptomycin and maintained at 37° C. in a 5% $CO_2$ atmosphere. Cells are passed by scraping the cells into suspension and sub-dividing them 1:4. After thawing, cells are passed serially no more than 12 times before new cells are removed from the cell repository.

2. Reagents and Preparation:

Dissolve BPM at a concentration of 1 mg/ml in pyrogen free saline for 20–24 hours at 4° C. Prior to use serial dilute in high glucose Dulbecco's modified Eagle's (DME) media supplemented with 10% FBS and 1% P/S. Likewise, dissolve recombinant mouse IFN- (obtained from Genzyme, Inc., Cambridge, Mass.) in high glucose DME medium supplemented with 10% FBS and 1% P/S immediately prior to use. Prepare Griess reagent anew for each use mixing equal volumes of Solution A and B. Solution A: 0.1% Naphthylene-diamine dihydrochloride dissolved in water. Solution B: 1% Sulfanilamide dissolved in 2.5% solution of $H_3PO_{4(85\%)}$. Griess reagent is stable for 12 hours at 4° C. Solutions A and B are stable at 4° C. for two months.

3. Method:

Grow RAW 264.7 cells in DMEM supplemented with 10% FBS and 1% P&S.

Scrape and count cells. Suspend at $10^5$ cells/ml.

Seed cells in a 96 well culture plate at $10^4$ cells/well (0.1 ml of the cell suspension) and allow to attach for 3 hours.

Remove culture media after attachment and add 0.1 ml media containing test material ("TM") (12.5, 25, 50, 100, 200, 400 µg/ml) or a TM/IFN- combination (12.5, 25, 50, 100, 200, 400 µg/ml and 10 U/ml of IFN-). In addition, add 10 U of IFN- to six additional wells and media alone to four more wells (controls). In addition, add 0.1 ml of serial dilutions of sodium nitrite (12.5, 25, 50, 100, 200 and 400) to duplicate wells for the purpose of generating a standard curve.

Incubate plate for 48 hours in a 5% $CO_2$ atmosphere at 37° C.

After incubation, remove 0.05 ml from each well and transfer to a new 96 well plate.

Add 0.05 ml of Greiss reagent to each test well.

Allow the reaction of the Greiss reagent with nitrite ions to proceed from 10–15 minutes.

Read plate at 590 nm using a Dynatech ELISA reader.

B. PROTOCOL OF MOUSE PULMONARY INFLAMMATION MODEL

Procedure:

1. Prepare endotoxin by dissolving in saline to achieve the desired concentration.

2. Anesthetize mouse. Instill 50 µl endotoxin directly into trachea or drop onto the nose of the mouse.

3. At the appropriate time of assessment, euthanize the mouse with an overdose of Sleepaway or an overdose of pentobarbital. Weigh the mouse. Expose the trachea, insert a catheter into the trachea—remove needle and push in slightly the teflon catheter.

4. Wash the lungs with five 1 ml washes of PBS. Pool the lavage fluid into a polypropylene conical tube.

5. From the pooled lavage fluid remove 200 µl of well mixed fluid and place in the Cytospin for 5 minutes at about 180 g. Stain with Diff-Qwik (Baxter) count for differential analysis of cells.

6. Centrifuge the pooled lavage fluid for 5 minutes at 180 g. Remove supernatant down to 1 ml of fluid. Re-suspend the cells in the remaining 1 ml.

7. Make a 1/10 dilution of the re-suspended lavage fluid to white cell diluting fluid (3% glacial acetic acid colored pale with Gentian violet). Count the cells on a Hemacytometer. Multiply the number of cells counted by 25,000 to achieve the total number of cells retrieved from washing the lungs.

C. MYELOPEROXIDASE ("MPO") ASSESSMENT OF LAVAGE FLUID AND TISSUES

Procedure:

I. Lavage Fluid

1. After removing the 40 µl of cells for the cell count, centrifuge the cells at about 180 g for approximately 5 minutes.

2. Remove and discard supernatant.

3. Add 9 ml of cold distilled water to lyse the RBC's. Mix gently to re-suspend the pelleted cells. Within 6–8 seconds add 3 ml of 3.8% NaCl and mix gently. (may have to repeat if too many RBC's are in the lavage)

4. Centrifuge at about 180 g for about 5 minutes.

5. Remove and discard supernatant. Assess for RBC content, if too many are present repeat steps 3–4.

6. Re-suspend the pelleted WBC's with 1 ml of 0.5% HTAB in 50 mM potassium phosphate buffer (HTAB).

7. Freeze-Thaw the samples 3 times.

8. Centrifuge the samples at about 180 g for approximately 5 minutes.

9. See Part III. below.

II. Tissue MPO Assessment

1. Macerate tissues in a polypropylene petri dish. Wash tissue into a Potter-Elvejhem tissue grinder with 1 ml of HTAB.

2. Grind tissue for 10 minutes. Assess thoroughness of grinding.

3. Wash tissue grinder with 2 additional ml of HTAB.

4. Freeze-thaw 3 times.

5. Remove 1 ml of the sample and centrifuge at about 35,000 g for about 20 minutes.

6. See Part II. below.

III. MPO Reaction

1. In a 96 well flat bottom ELISA plate add 100 µl of TMB microwell substrate (Kirkegaard-Perry) per well for each sample.

2. Each sample will be measured in triplicate.

3. Add 10 µl of the supernatant from the appropriate samples. Tap the ELISA plate gently to mix the substrate with the sample for 2 minutes.

4. Read on an ELISA reader at 405 nm.

D. MOUSE CROTON OIL EAR INFLAMMATION MODEL

Methods:

Adult male mice (30 g, HA-ICR, Frederick, Md., 10 animals/group) were given topically 25 µg/10 µl croton oil (2.5 mg croton oil/ 1 ml acetone) on the inner and outer surface of the right ear at zero time with a Hamilton microsyringe. The left ear was untreated since acetone produces no change on the ear. The difference between the inflamed and control ear was calculated. Test sample was applied 30 minutes after the irritant at 1 to 900 µg. The untreated and treated ear punch samples (6 mm) were removed and weighed 6 hours later. The results were recorded as % inhibition of ear swelling. A dose-response curve was constructed for each Factor tested.

E. PROTOCOL FOR CYTOKINE ANALYSIS FROM MACROPHAGES MOUSE TNF-α ASSAY IN BIOLOGICAL FLUIDS

IL-1α Determination of the TNF-α Content in Tissue Culture Fluids (1) RAW cells are treated in the presence of different concentrations of different fractions of either acemannan, interferon-γ, acemannan/IFN-γ or medium for 24 hours. (2) The culture supernatants are stored at −20° C. until testing begins. (3) 0.50 μl of each sample is mixed with 0.50 μl of wash buffer and added to each well. The plate is sealed with an adhesive cover and incubated for 2 hr at 37° C. (4) The liquid is removed by inverting the plate. Wash plate 4× (each wash 10 mins) in wash buffer. (5) Blot plate dry on paper towels. 100 μl of HRP-Conjugated anti-mouse TNF-α is added into each well, the plate sealed and incubated at 37° C. for 1 hour. (6) Remove the liquid by inverting the plate, was 4× (each was 10 mins). Blot plate dry on paper towels. (7) Mix equal volumes of reagent A and B to yield the substrate solution 10 mins before use. 100 μl of substrate solution is added into each well and incubated at room temperature for 10 mins. Stop color development by add 100 μl of stop solution per well. (9) Read the absorbance at 450 nm.

IL-1α is tested in a similar manner as TNF manufactures using ELISA Kit Methodology.

Cytokine IL-6 Assay. Determination the IL-6 Content of Biological Fluid Using a Dot Blot Technique (1) RAW cells are cultured on 96-flat-well plate for 24 hours at a density of $10^9$ cells/well. The supernatants are removed and stored at −70° C. for testing the cytokine production. (2) Pre-wet a PVDF membrane in methanol for 30 seconds. The membrane is placed in TBS-0.05% between buffer for 5 minutes. Assemble the Bio-dot apparatus. Make sure all screws have been tightened under vacuum to insure that there will not be any cross-well contamination. (3) 200 μl of samples are loaded onto each well. The entire sample is filtered through the membrane by gentle vacuum. 200 μl of TBS buffer were added to wash each well and filtered again. (4) After the well has been completely drained, remove the membrane from the apparatus. (5) Place the membrane in the blocking solution (3% BLOTTO in TBS-0.05%) at 4° C. overnight. (6) The membrane is washed in TS-0.05% between buffer 3 times (10 minutes each). Then, incubated in anti-murine IL-6 antibody (goat IgG) (1:1000 in 1% BLOTTO TBS/0.05% between buffer) (From R&D) for 2 hours at room temperature with gentle shaking. (7) Wash the membrane again 3 times in TBS-0.05% buffer, then incubate in antigoat-IgG-AP for 2 hours at 1:30,000 in 1% BLOTTO-TBS/0.05% buffer, then incubate in antigoat-IgG-AP for 2 hours at 1:30,000 in 1% BLOTTO-TBS/0.05% between) with gentle shaking. (8) Wash the membrane 3 times in washing buffer, the last time wash was in TBS buffer. (9) Color is developed in the alkaline phosphate substrate solution until the dots can be clearly seen. Wash the membrane in water and then air dry.

EXAMPLE 6

CENTRIFUGATION OF SUSPENSION OF RESULTS OBTAINED FROM BIOASSAYS USED TO EVALUATE DIFFERENT FACTORS (1) 1k pellet: the pellet following centrifugation at about 180 g value for 10 minutes. Amount: ~5% by weight. Appearance: bright crystal-like materials of various shapes under microscope; more than half of them were needle-like with sharply-defined edges.

(2) 1–12k pellet: the pellet following centrifugation of the 1k supernatant at about 20,000 g for 30 minutes. Amount: 10–15% by weight. Appearance: whitish cloudy solution after suspension; fine particulate materials (~1 μm) under microscope. All the protein binding activities were detected through these molecules. They were most potent in induction of NO from macrophages; proteins from serum (including vitronectin) bound to them were highly mitogenic to NIH 3T3 fibroblasts.

(3) 12k supernatant: the supernatant following centrifugation at about 20,000 g for 30 minutes. Amount: 70–80% by weight after lyophilization. Appearance of the solution: nearly clear (the original solution before centrifugation was whitish and cloudy); no visible particulate materials under microscope. This "Factor" appeared to contain molecules that were fully soluble. It was much less potent in inducing NO from macrophages compared to the 1–12k "Factor."

Conclusion: Separation of different Factors by centrifugation yield as optimal macrophage activating Factor between 180–20,000 g. Soluble Factors after centrifugation had potent anti-inflammatory activity.

EXAMPLE 7

RESULTS FROM FACTORS USING METHODS AS DESCRIBED

To understand the effects of FBA on macrophages and the functions of different Factors obtained from the original FBA, several cytokines including IL-6, IL-1α and TNF have been tested on fresh peritoneal macrophages. As used in experiments in this example, "soluble Factor" is used to denote one or more Factors of FBA obtained by centrifugating FBA suspended in water at (about 25,000 g) for about 1 hour, the supernatant obtained was conveniently given the name "soluble Factor"; one or more Factors in pellet form obtained from this centrifugation was conveniently given the name "pellet Factor."

IL-6 Production:

It has been shown by Dot blot that RAW cells responded in a dose dependent manner to FBA in regards to IL-6 production. Both the "original product" and separated "pellet Factor" are potent factors in stimulating RAW cell released IL-6 production. In contrast to this result, "soluble Factor" had a minimum effect on IL-6 production. To understand the biological functions of these two different Factors, the competition experiments were performed using constant amount of "pellet Factor" with increasing amount of "soluble Factor," results showed that the amount of IL-6 production was decreased along with the increased amount of "soluble Factor." This indicated that "soluble-Factor" and "pellet Factor" had different roles on macrophages.

To understand the above effects, phagocytosis experiments were conducted using constant Flouroscein isothiocyanate ("FITC") labeled pellet Factor with increasing amounts of unlabeled "soluble Factor." Results showed that macrophages phagocytosed less FITC-labeled "pellet Factor" along with increasing amount of "soluble Factor." Together, results suggested that "soluble Factor" might have competitive or inhibitory effects with "pellet Factor".

IL-1α Productions:

The production of IL-1α were tested by Dot Blot using 5% paraformaldehyde fixed RAW cells. Results showed that IL-1α was constitutively expressed by RAW cells. In addition, results showed that "soluble Factor," "pellet Factor" and "original FBA" had the same effects on IL-1α production (the amount of IL-1α was the same as control).

EXAMPLE 8

MICROPARTICULATE FACTOR FROM FBA AND NO PRODUCTION

Materials and Methods:

Factor Preparation: 40 mg of FBA was dissolved as suspended in 20 ml pyrogen-free water and centrifuged in two identical 20 ml portions at about 180 g for about 10 minutes and then at about 25,000 g for about 30 minutes. One pellet was suspended in a small amount of DMEM with 10% FBS, and another suspended in water and lyophilized. The dried pellet weighed 2.2 mg, and this number was used to adjust the pellet suspended in DMEM to 1 mg/ml. The 1 mg/ml soluble FBA solution in DMEM was prepared from lyophilized 25,000 g or 155,000 g centrifugation supernatant.

NO assay: performed under standard conditions without interferon using Raw cells.

Results:

The NO assay results showed that the "microparticulate Factor" ("MF") (see below) was a strong stimulator of macrophage on its own. Significant NO production started to be seen at 12.5 μg/ml. The higher the "microparticulate Factor" concentration, the higher the level of NO produced. The NO production was associated with corresponding cell morphological changes that indicate macrophage activation.

The repeated experiments showed the same results. The effect of the MF on NO production was stronger than that produced by zymosan which is a microparticulate carbohydrate (3–5 μm) from yeast (Sigma Chemicals Co.).

The 25,000 g and 155,000 g supernatant or "soluble Factors" had no effect on NO production or cell morphology, being consistent with previous observations. In the Table, "MF" means "microparticulate Factor" derived as the pellet from centrifugation at about 25,000 g for about 30 minutes after 180 g (10 minutes) pellet (crystal-like material) has been discarded. "SF-1" Factor is the supernatant Factor after 25,000 g centrifugation for about 30 minutes. "SF-2" Factor is the supernatant Factor after 150,000 g centrifugation for about 30 minutes.

Conclusion: Macrophage activation is associated with the "microparticulate Factor."

"SOLUBLE FACTOR" AND "MICROPARTICULATE FACTOR" FROM FBA - NO ASSAY RESULTS

| μG/M1 | MF | | SF-1 | | SF-2 | |
|---|---|---|---|---|---|---|
| 0 | 0.032 | 0.03 | 0.03 | 0.027 | 0.026 | 0.028 |
| 1.56 | 0.031 | 0.027 | 0.03 | 0.027 | 0.027 | 0.031 |
| 3.125 | 0.031 | 0.03 | 0.026 | 0.024 | 0.025 | 0.027 |
| 6.25 | 0.046 | 0.039 | 0.03 | 0.032 | 0.026 | 0.026 |
| 12.5 | 0.063 | 0.056 | 0.025 | 0.032 | 0.029 | 0.024 |
| 25 | 0.095 | 0.099 | 0.037 | 0.035 | 0.026 | 0.03 |
| 50 | 0.133 | 0.124 | 0.031 | 0.029 | 0.025 | 0.027 |
| 100 | 0.156 | 0.166 | 0.035 | 0.033 | 0.03 | 0.028 |
| 200 | 0.196 | 0.189 | 0.033 | 0.033 | 0.027 | 0.025 |
| 400 | 0.211 | 0.223 | 0.043 | 0.037 | 0.027 | 0.029 |

| | Average | | |
|---|---|---|---|
| | MF | SF-1 | SF-2 |
| 0 | 0.031 | 0.0285 | 0.027 |
| 1.56 | 0.029 | 0.0285 | 0.029 |
| 3.125 | 0.031 | 0.025 | 0.026 |
| 6.25 | 0.0425 | 0.031 | 0.026 |
| 12.5 | 0.0595 | 0.0285 | 0.0265 |
| 25 | 0.097 | 0.036 | 0.028 |
| 50 | 0.1285 | 0.03 | 0.026 |
| 100 | 0.161 | 0.034 | 0.029 |
| 200 | 0.1925 | 0.033 | 0.026 |
| 400 | 0.217 | 0.04 | 0.028 |

"MICROPARTICULATE FACTOR" FROM FBA AND ZYMOSAN - NO ASSAY

| μg/ml | MF | | SF-1 | | Zymosan | |
|---|---|---|---|---|---|---|
| | OD570 | OD570 | OD570 | OD570 | OD570 | OD570 |
| 0 | 0.022 | 0.022 | 0.022 | 0.022 | 0.022 | 0.022 |
| 25 | 0.08 | 0.072 | 0.025 | 0.026 | 0.033 | 0.038 |
| 50 | 0.117 | 0.112 | 0.024 | 0.022 | 0.057 | 0.052 |
| 100 | 0.129 | 0.125 | 0.026 | 0.022 | 0.093 | 0.086 |
| 200 | 0.14S | 0.145 | 0.025 | 0.023 | 0.127 | 0.131 |
| 400 | 0.165 | 0.167 | 0.03 | 0.024 | 0.162 | 0.155 |

| | Average | | |
|---|---|---|---|
| | MF | SF-1 | zymosan |
| 0 | 0.022 | 0.022 | 0.022 |
| 25 | 0.076 | 0.026 | 0.036 |
| 50 | 0.115 | 0.023 | 0.055 |
| 100 | 0.127 | 0.024 | 0.09 |
| 200 | 0.147 | 0.024 | 0.129 |
| 400 | 0.168 | 0.027 | 0.159 |

EXAMPLE 9

MACROPHAGE ACTIVATION AND ANTI-INFLAMMATORY ACTIVITIES

FBA was dissolved and suspended in saline or DMEM at 1 mg/ml. It was then sized by centrifugation into three Factors: "MF" as defined above, "SF-1" as defined above and the original FBA.

Epitheleal Cells ("EC") Proliferation

The three factors from above reconstituted in saline were used in an epithelial cell (EC) proliferation assay with bovine coronary EC. Results showed that (1) the MF was much more potent than the "SF-1" in stimulating EC proliferation; (2) the SF-1 at 10 μg/ml exhibited inhibitory effect that was not seen with the original FBA at the same concentration.

IL-6 Assay

The three factors from above in DMEM were used for IL-6 assay using mouse macrophages (RAW cells). The result showed that the "MF" stimulated IL-6 production and the SF-1 had minimal or no effect.

The discarded crystal-like 180 g pellet was included in NO assays, and its effect was minimal compared to the "MF".

RAW Cells Secreted Interleukin-6 in Response to FBA

To determine if RAW cells could produce IL-6 response to FBA, they were cultured in the presence of different concentrations of FBA (12.5 to 400 μg/ml) for 4, 10, 24, and 48 hours. The culture supernatants were removed and tested for cytokine production. Results showed that FBA could stimulate RAW cells to produce IL-6. The IL-6 could be detected by 10 hours. Maximum IL-6 production was at 24 hours post-stimulation. This IL-6 production was dose dependent. The production of IL-6 did not require costimulation with interferon. Results suggested that FBA was an effective macrophage activating component in stimulating RAW cell IL-6 production.

"MF" Stimulated IL-6 Production

RAW cells were stimulated by different Factors prepared from FBA. Results showed that MF could stimulate IL-6 production in RAW cells in a dose-dependent manner. SF-1 had minimum effects on IL-6 production.

The results of these investigations show that, in general, the two Factors have opposing biological activities. The "MF" activates macrophages stimulating both NO and IL-6 production. It also stimulates proliferation of vascular endothelial cells. It is proinflammatory in the mouse lung model. It has no effect on neutrophil adherence to vascular endothelial cells.

In contrast, SF-1 appears to have no effect on macrophage function in that it does not stimulate NO or IL-6 production. It does, however, inhibit vascular cell proliferation, inhibit neutrophil adherence to these cells, and has anti-inflammatory activity, as shown in the Mouse-Pulmonary Inflammation Model.

EXAMPLE 10

ANTI-INFLAMMATORY ACTIVITIES OF "SOLUBLE FACTORS"

FBA was dissolved in saline at 1 mg/ml and then sized either by centrifugation or filtration into two Factors: "Soluble Factor" from centrifugation ("SF-1"), and "soluble Factor" filtered through a 0.1 $\mu$m filter ("SF-3"). The mice received 1 mg IP of either SF-1 or SF-2 or saline as a control. At time of sacrifice, both the SF-1 and SF-2 had significantly less number of cells and neutrophils as well as less MPO than the control group that received only saline. The results suggested that SF-3 had a better effect than SF-1.

Conclusion: Centrifugation or filtration can be utilized to size FBA to yield a potent anti-inflammatory Factor.

EXAMPLE 11

FILTRATION WITH 0.1 $\mu$m FILTERS OF "MICROPARTICLE FACTORS"

Procedure:

1. 100 mg of FBA was dissolved/suspended in 100 ml pyrogen-free water to give a 1 mg/ml solution/suspension.

2. Filters. Syringe filters with a pore size of 5, 2, 1.2, 0.8, 0.45, 0.2, or 0.1 $\mu$m were obtained from Baxter.

3. Filtration. 40 ml of the 1 mg/ml FBA solution/suspension was sequentially filtered through all 8 filters described above from 5 $\mu$m to 0.1 $\mu$m. The solution was passed through the 0.1 $\mu$m filters twice at the end. 30 ml of the final filtrate was centrifuged at about 25,000 g for about 30 minutes. As controls for the supernatant carbohydrate content, 30 ml of the original acemannan solution/suspension was centrifuged directly at about 25,000 g for about 30 minutes, and another 30 ml was filtered through the 5 $\mu$m filters before the centrifugation step.

4. Anthrone assay. The 0.2% anthrone reagent (Sigma) was prepared freshly in concentrated sulfuric acid. 100 $\mu$l of the reagent was mixed with each 50 $\mu$l filtrate or centrifugation supernatant (diluted 3x) in 96-well plates. The multiple channel pipette aid was used to ensure all samples were mixed in the same manner, minimizing variations during the mixing step. After incubation at room temperature for 15 minutes, the $OD_{630\ nm}$ values were determined using a ELISA reader.

Results:

The final filtrate obtained by the sequential filtration appeared to be as clear as water. When the filtrate (30 ml) was centrifuged at about 25,000 g for about 30 minutes, no pellet was detected. The experiments were repeated once with the same results obtained. This indicates that the "MF" can be removed by this sequential filtration scheme.

The carbohydrate content in filtrate obtained by sequential filtration did not show any apparent differences as compared to the 25,000 g and 5 $\mu$m/25,000 g supernatant. This indicates that the sequential filtration does not remove any "soluble carbohydrates."

In summary, these results showed that the filtration method can be used to size FBA into the "MF" and "SF-1" Factors.

EXAMPLE 12

FACTORS OF FBA SIZED FILTRATION THROUGH SYRINGE FILTERS OF VARIOUS PORE SIZES

Material and Methods:

1. Factors Preparation:

200 mg of FBA was dissolved/suspended in 200 ml pyrogen-free water to give a 1 mg/ml solution/suspension. The solution/suspension was filtered sequentially through 5, 2, 1.2, 0.8, and 0.45 $\mu$m syringe filters (10 ml/filter). After each filtration step, 30 ml filtrate was taken and centrifuged at about 25,000 g for about 30 minutes. Factors in pellets were collected, lyophilized, and weighed. A 200 $\mu$l sample was also taken after each filtration step for total carbohydrate determination by anthrone assay.

| Filters($\mu$m) | Original | 5 | 2.0 | 1.2 | 0.8 | 0.45 |
|---|---|---|---|---|---|---|
| FBA solution/suspension (ml) | 30 | 30 | 30 | 30 | 30 | 30 |

2. Anthrone Assay:

The 0.2% anthrone reagent (Sigma) was prepared freshly in concentrated sulfuric acid. A 100 $\mu$l of the reagent was mixed with each 50 $\mu$l filtrate sample (diluted 3x) in 96-well plates. The multiple channel pipette aid was used to ensure all samples were mixed in the same manner, minimizing variations during the mixing step. After incubation at room temperature for 15 minutes, the $OD_{630\ nm}$ values were determined using a ELISA reader.

Results:

1. The amount of Factor(s) in pelletable materials and in the filtrate was determined.

The amount of 25,000 g for 30 minutes pelletable materials solution/suspension Factor(s) decreased following sequential filtration with syringe filters of various pore sizes (see Table). After 0.45 $\mu$m, 81% of the total Factor in pelletable materials were removed. The major decrease occurred between 1.2–0.8 $\mu$m, and the smallest one between 5 and 2 $\mu$m. These observations are consistent with the estimated size (~1 $\mu$m) of the "microparticle Factor." However, there are some particles of smaller sizes, since nearly 19% of the Factor in pelletable materials passed through the 0.45 μm filters. A complete removal of Factor in pelletable materials was therefore not obtained with these filters. However, all pelletable material could be removed after filtration through a 0.1 μm filter.

| Filters(μm) | Original | 5 | 2.0 | 1.2 | 0.8 | 0.45 |
|---|---|---|---|---|---|---|
| Volume | 30 | 30 | 30 | 30 | 30 | 30 |
| Weight (mg) of 25,000 g, 30 min pellet | 3.5 | 2.3 | 2.1 | 1.7 | 1.1 | 0.7 |

2. Carbohydrate Content in the Filtrate

The carbohydrate content in Factor found in the filtrate did not show significant changes as compared to the original solution (unfiltered) based on anthrone assays. This suggests that except for removing Factor in microparticulate materials, sizing using above-listed filters did not remove any soluble Factor.

Results:

1) The 5 μm filtration removed ~36% of the total pelletable materials (~3.3 mg out of 30 mg). The 180 g centrifugation (10 min) removed ~26% of the total pelletable materials. Considering that the 180 g pellet contains mainly the fiber-like "unusable" materials, the 5 μm filtration has preserved the majority of the effective materials-microparticles, i.e., 85% (2.1 mg/2.5 mg) (see Table below).

Discussion:

These experiments showed that the 5 μm filters can be used to size the Factor similarly to the 180 g centrifugation (10 min) that separates the fiber-like materials. After the 5 μm filtration, 2.3 mg of the total 3.5 mg of Factor in pelletable materials 25,000 g centrifugation (30 min) were retained, removing 1.2 mg of Factor materials which is slightly more than Factor in 180 g materials (10 min) (0.91 mg, which accounts for 26% of the total pelletable materials).

Conclusion:

Although 5 μm filtration is similar to 180 g centrifugation (10 min) in removal of fiber-like pelletable material depending on shape/size and chemical equilibrium in the suspension/solution. It varies in the amount of recoverable material suggesting that filtration may be a more accurate means of separating Factors.

EXAMPLE 13

FACTORS SIZED AND ISOLATED BY 5 μm FILTRATION AND NO ASSAY

Materials and Methods:

FBA

Filters: Gelman Acrodisc 5 μm sterile syringe filter, non pyrogenic, and 25 mm in diameter.

Filtration: 100 mg of FBA was dissolved/suspended in 100 ml water to give a 1 mg/ml solution/suspension. The solution/suspension was divided into three 30 ml portions and processed as follows: 1) Centrifuged at about 180 g for about 10 minutes and 25,000 g for 30 minutes, and the 1k and 18k pellets collected. 2) Filtered through 5 μm syringe filters (10 ml/filter) and then centrifuged at 25,000 g for 30 minutes, and the pellet collected. 3) Centrifuged directly at 25,000 g for 30 minutes and the pellet collected. All pellets were lyophilized and weighed.

NO assay: 10 mg of FBA was dissolved in 10 ml DMEM without serum. 5 ml was filtered through the 5 μm filter. Both filtered and unfiltered were tested at 400, 200, and 100 μg/ml for NO production in the presence or absence of interferon using Raw cells.

|  | Filtered | | 1–18k pellet | |
|---|---|---|---|---|
|  | Direct 18k pellet | 18k pellet | 1k pellet | 1–18k pellet |
| Weight | 3.0 mg | 2.1 mg | 0.9 mg | 2.5 mg |
| % removal | 0% | 36% | N/A | 26% |
| % preserved | 100% | 64% | N/A | 74% |

2) Under the microscope, the 25,000 g pellet materials from 5 μm filtered FBA were uniformly microparticles with no fiber-like material. The quality of this preparation appears to be better than that of "MF" in that the latter does contain trace amount of fiber-like materials. The better quality is likely due to a more uniform sizing.

3) NO assay results showed that the filtered FBA kept 84% of the original activity of the unfiltered FBA. This result is consistent with the amount of the microparticulate FBA left (85%; 2.1 mg/2.5 mg) after filtration as described above.

Together, these experiments showed that the 5 μm filter can be used to remove the fiber-like materials, and at the same time, have the majority of "macrophage activation" or NO production activity preserved.

CARBOHYDRATE CONTENT IN "SOLUTION FACTORS" OF
FBA SEQUENTIAL FILTRATION ON (5,2,1.2,0.8,0.45 μm Filters)

| | EXP I | | | | | EXP II | | |
|---|---|---|---|---|---|---|---|---|
| μg/ml | Average | OD630 | OD630 | OD630 | μg/ml | Average | OD630 | OD630 |
| 0 | 0.0105 | 0.01 | 0.011 | | 0 | 0.016 | 0.013 | 0.019 |
| 31.25 | 0.061 | 0.053 | 0.069 | | 62.5 | 0.102 | 0.081 | 0.123 |
| 62.5 | 0.1095 | 0.096 | 0.123 | | 125 | 0.1775 | 0.157 | 0.198 |
| 125 | 0.1965 | 0.165 | 0.228 | | 250 | 0.3285 | 0.291 | 0.366 |
| 250 | 0.3835 | 0.362 | 0.405 | | 500 | 0.6015 | 0.553 | 0.65 |
| 500 | 0.5775 | 0.624 | 0.531 | | 1000 | 1.0335 | 0.941 | 1.126 |
| 1000 | 1.131 | 1.114 | 1.148 | | original | 0.27 | 0.27 | 0.27 |
| 200 | 0.346667 | 0.334 | 0.335 | 0.371 | 5 μm | 0.268 | 0.263 | 0.273 |
| 200 | 0.343667 | 0.344 | 0.325 | 0.362 | 2 μm | 0.293 | 0.301 | 0.285 |
| 200 | 0.346333 | 0.362 | 0.323 | 0.354 | 1.2 μm | 0.2535 | 0.263 | 0.244 |
| 200 | 0.323333 | 0.303 | 0.319 | 0.348 | 0.8 μm | 0.2755 | 0.29 | 0.261 |
| 200 | 0.308333 | 0.303 | 0.286 | 0.336 | 0.45 μm | 0.259 | 0.255 | 0.263 |
| 200 | 0.339333 | 0.343 | 0.323 | 0.352 | | | | |

| FBA FILTERED THROUGH 5 µm FILTERS - NO ASSAY | | | | | | | | | | |
|---|---|---|---|---|---|---|---|---|---|---|
| | unfiltered | | unfiltered W/IFN | | Filtered | | Filtered w/IFN | | Average | | |
| µg/ml | OD570 | OD570 | OD570 | OD570 | OD570 | OD570 | OD570 | OD570 | unfiltered | unfiltered | Filtered |
| 100 | 0.029 | 0.026 | 0.099 | 0.109 | 0.023 | 0.026 | 0.087 | 0.093 | 0.0275 | 0.104 | 0.0245 |
| 200 | 0.05 | 0.051 | 0.139 | 0.13 | 0.038 | 0.032 | 0.11 | 0.117 | 0.0505 | 0.1345 | 0.035 |
| 400 | 0.084 | 0.082 | 0.214 | 0.214 | 0.08 | 0.069 | 0.166 | 0.174 | 0.083 | 0.214 | 0.0745 |

EXAMPLE 14

TOPICAL ANTI-INFLAMMATORY ACTIVITY OF FREEZE-DRIED ALOE VERA EXTRACT AND FBA

Methods:

The croton oil mouse ear inflammatory model described earlier was used to evaluate several different Factors.

Results and Discussion:

The % inhibition of freeze dried aloe vera extract (Manapol® powder) on the dose-response curve increased from 5.8±0.4% at 1 µg to a maximum of 50.0±4.3% at 270 µg. The later response marked the beginning of a short plateau. At 300 µg, the % inhibition decreased from 50.2±7.9 to 29.6±2.8 (600 µg) to 18.6±1.8 (900 µg). This "drop off" after the plateau represents a 62% reduction from the maximum response. This type of response is characteristic of many biologic response modifiers. See, Tables below.

The anti-inflammatory response of BPM did not begin to increase until the dose of 33 µg was topically applied. This means that compared to the freeze dried aloe vera extract, the curve has shifted to the right indicating reduced activity. The maximum plateau response for BPM was 33.9±2.9% as compared to 50.2±7.9 for the aloe vera extract powder. Also, the plateau was reached at a smaller dose for the extract (270 µg) as compared to BPM (600 µg). These data indicate that both products gave good dose response curves but that Freeze dried aloe vera abstract (a Factor) produced better topical anti-inflammatory activity than did BPM.

| DOSE RESPONSE CURVE OF ALOE VERA EXTRACT TOPICAL ANTI-INFLAMMATORY ACTIVITY USING THE CROTON OIL EAR SWELLING ASSAY | |
|---|---|
| Dose µg/10 µl | Inhibition % |
| 900 | −18.6 ± 1.8 |
| 600 | −29.6 ± 2.8 |
| 300 | −50.2 ± 7.9 |
| 270 | −50.0 ± 4.3 |
| 100 | −46.6 ± 4.0 |
| 90 | −46.3 ± 4.4 |
| 30 | −34.8 ± 2.1 |
| 10 | −25.0 ± 2.0 |
| 1 | −5.8 ± 0.4 |

10 mice/group. 25 µg/10 µl croton oil. ± = S.E.

| DOSE RESPONSE CURVE OF BPM TOPICAL ANTI-INFLAMMATORY ACTIVITY USING THE CROTON OIL EAR SWELLING ASSAY | |
|---|---|
| Dose µg/10 µl | Inhibition % |
| 900 | −22.0 ± 0.6 |
| 600 | −33.9 ± 2.9 |
| 300 | −27.5 ± 1.7 |
| 100 | −18.4 ± 1.1 |
| 33 | −11.3 ± 0.7 |
| 10 | 0.0 ± — |
| 1 | 0.0 ± — |

10 mice/group. 25 µg/10 µl croton oil. ± = S.E.

While preferred methods for obtaining different bioactive Factors from aloe have been disclosed, it will be apparent to those skilled in the art that numerous modifications and variations are possible in light of the above teaching. It should also be realized by those skilled in the art that such modifications and variations do not depart from the spirit and scope of the invention as set forth in the appended claims.

What is claimed is:

1. A method of producing a Factor from aloe, said Factor being analgesic, antiviral, antinflammatory, antineoplastic, immune stimulating, immune modulating or adjuvant, said method comprising the steps of:

filtering a starting material with a course filter, having a pore size ranging from about 400 µm to about 800 µm, to give a coarsely-filtered starting filtrate, said starting material being selected from the group consisting of a crushed aloe leaf, aloe gel fillet, aloe raw gel, and dried aloe vera gel extract;

filtering said coarsely-filtered starting filtrate with a medium filter, having a pore size ranging from about 100 µm to about 400 µm, to give a mediumly-filtered starting filtrate; and sizing said mediumly-filtered starting filtrate with a method selected from the group consisting of pH adjustment, selective precipitation, centrifugation, ultracentrifugation, irradiation, filtration, ultrafiltration, homogenizing, and combination thereof.

2. The method of claim 1 further comprising the step of sizing by chromatography and combination thereof.

3. The method of claim 1 further comprising the step of sizing by dialysis and combination thereof.

4. The method of claim 1 further comprising the step of compounding said Factor with another compound or mixture of compounds from aloe.

5. A method of producing a Factor from aloe, said Factor being analgesic, antiviral, antinflammatory, antineoplastic, immune stimulating, immune modulating or adjuvant, said method comprising the steps of:

filtering a starting material with a course filter, having a pore size ranging from about 400 µm to about 800 µm, to give a coarsely-filtered starting filtrate, said starting material being selected from the group consisting of a crushed aloe leaf, aloe gel fillet, aloe raw gel, and dried aloe vera gel extract;

filtering said coarsely-filtered starting filtrate with a medium filter, having a pore size ranging from about 100 μm to about 400 μm, to give a mediumly-filtered starting filtrate; and step-wise filtering said mediumly-filtered starting filtrate using filters having progressively smaller pore sizes to give a filtrate Factor and a retentate Factor.

6. The method of claim 5 further comprising the step of:

sizing said filtrate Factor with a method selected from the group consisting of pH adjustment, selective precipitation, centrifugation, ultracentrifugation, irradiation, chromatography, dialysis, filtration, ultrafiltration, homogenizing, and combination thereof.

7. The method of claim 5 further comprising the step of:

sizing said retentate Factor with a method selected from the group consisting of pH adjustment, selective precipitation, centrifugation, irradiation, chromatography, dialysis, filtration, ultrafiltration, homogenizing, and combination thereof.

8. The method of claim 5 further comprising the steps of:

filtering said mediumly-filtered starting filtrate using a filter having a pore size ranging from about 25 μm to about 100 μm giving a first retentate Factor and a first filtrate Factor;

filtering said first filtrate Factor using a filter, having a pore size ranging from about 5 μm to about 25 μm, to give a second retentate Factor and a second filtrate Factor; and filtering said second filtrate Factor using a filter, having a pore size ranging from about 1 μm to about 5 μm, to give a third retentate Factor and a third filtrate Factor.

9. The method of claim 8 further comprising the step of filtering said third filtrate Factor using a filter, having a pore size ranging from about 0.1 μm to about 1 μm, to give a fourth retentate Factor and a fourth filtrate Factor.

10. The method of claim 9 further comprising the step of filtering said fourth filtrate Factor using a filter, having a pore size ranging from about 0.04 μm to about 0.1 μm, to give a fifth retentate Factor and a fifth filtrate Factor.

11. The method of claim 5 further comprising the step of compounding said Factor with another compound or mixture of compounds from aloe.

12. A method of producing a Factor from aloe, said Factor being analgesic, antiviral, antinflammatory, antineoplastic, immune stimulating, immune modulating or adjuvant, said method comprising the steps of:

filtering a starting material with a course filter, having a pore size ranging from about 400 μm to about 800 μm, to give a coarsely-filtered starting filtrate, said starting material being selected from the group consisting of a crushed aloe leaf, aloe gel fillet, aloe raw gel, and dried aloe vera gel extract;

filtering said coarsely-filtered starting filtrate with a medium filter, having a pore size ranging from about 100 μm to about 400 μm, to give a mediumly-filtered starting filtrate; and filtering said mediumly-filtered starting filtrate with a fine filter, having a pore size ranging from about 0.04 μm to about 100 μm, to give a filtrate Factor and a retentate Factor.

13. The method of claim 12 further comprising the step of:

sizing said filtrate Factor with a method selected from the group consisting of pH adjustment, selective precipitation, centrifugation, ultracentrifugation, irradiation, chromatography, dialysis, ultrafiltration, homogenizing, and combination thereof.

14. The method of claim 12 further comprising the step of:

sizing said retentate Factor with a method selected from the group consisting of pH adjustment, selective precipitation, centrifugation, irradiation, chromatography, dialysis, ultrafiltration, homogenizing, and combination thereof.

15. The method of claim 12 further comprising the step of:

sizing said filtrate Factor with a water soluble, lower aliphatic polar solvent.

16. The method of claim 15, wherein said water soluble lower aliphatic polar solvent is ethanol.

17. The method of claim 12 further comprising the step of:

sizing said retentate Factor by selective precipitation with a water soluble, lower aliphatic polar solvent.

18. The method of claim 17, wherein said water soluble lower aliphatic polar solvent is ethanol.

19. The method of claim 12 further comprising the step of compounding said Factor with another compound or mixture of compounds from aloe.

20. A method of producing a Factor from aloe, said Factor being analgesic, antiviral, antinflammatory, antineoplastic, immune stimulating, immune modulating or adjuvant, said method comprising the steps of:

centrifugating a starting material to give a centrifugated starting supernatant and a centrifugated starting pellet, said starting material being selected from the group consisting of a crushed aloe leaf, aloe gel fillet, aloe raw gel, and dried aloe vera gel extract; and sizing said centrifugated starting supernatant with a method selected from the group consisting of pH adjustment, selective precipitation, ultracentrifugation, irradiation, chromatography, dialysis, filtration, ultrafiltration, homogenizing, and combination thereof.

21. The method of claim 20 further comprising the step of:

sizing said centrifugated starting pellet with a method selected from the group consisting of pH adjustment, selective precipitation, ultracentrifugation, irradiation, chromatography, dialysis, filtration, ultrafiltration, homogenizing, and combination thereof.

22. The method of claim 20, wherein said centrifugation is carried at below 100,000 g for a period of from about 10 minutes to about 48 hours.

23. The method of claim 20 further comprising the step of:

centrifugating said centrifugated starting supernatant at a range from about 100,000 g to about 150,000 g for a period of from about 10 minutes to about 48 hours.

24. A method of producing a Factor from aloe, said Factor being analgesic, antiviral, antinflammatory, antineoplastic, immune stimulating, immune modulating or adjuvant, said method comprising the steps of:

filtering a starting material with a filter, having a pore size ranging from about 100 μm to about 800 μm, to give a filtered starting filtrate, said starting material being selected from the group consisting of a crushed aloe leaf, aloe gel fillet, aloe raw gel, and dried aloe vera gel extract;

ultrafiltering said filtered starting filtrate to give an ultra-filtered filtrate having a molecular weight of greater than about 100 Daltons and a retentate having a molecular weight of greater than about 10,000 Daltons; and sizing said ultra-filtered filtrate with a method selected from the group consisting of pH adjustment, selective precipitation, dialysis, centrifugation, ultracentrifugation, irradiation, chromatography, homogenizing, and combination thereof.

25. The method of claim 24, further comprising the step of:

sizing said retentate with a method selected from the group consisting of pH adjustment, selective precipitation, dialysis, centrifugation, ultracentrifugation, irradiation, chromatography, homogenizing, and combination thereof.

26. A method of producing a Factor from aloe, said Factor being analgesic, antiviral, antiinflammatory, antineoplastic, immune stimulating, immune modulating or adjuvant, said method comprising the steps of:

filtering a bulk pharmaceutical mannan with a fine filter, having a pore size ranging from about 0.04 $\mu$m to about 100 $\mu$m, to give a filtered starting filtrate;

irradiating said filtered starting filtrate with a gamma radiation in an amount from about 2 MRad to about 15 MRad to give a filtered and irradiated Factor; and sizing said filtered and irradiated Factor with a method selected from the group of centrifugation, ultracentrifugation, chromatography, further irradiation, dialysis, filtration, ultrafiltration, and combination thereof.

27. A method of producing a Factor from aloe, said Factor being analgesic, antiviral, antiinflammatory, antineoplastic, immune stimulating, immune modulating or adjuvant, said method comprising the steps of:

centrifugating a bulk pharmaceutical mannan to give a centrifugated starting supernatant and a centrifugated starting pellet; and sizing said centrifugated starting supernatant with a method selected from the group consisting of irradiation, centrifugation, ultracentrifugation, chromatography, dialysis, filtration, ultrafiltration, homogenizing, and combination thereof.

28. The method of claim 27 further comprising the step of:

sizing said centrifugated starting pellet with a method selected from the group consisting of irradiation, centrifugation, ultracentrifugation, chromatography, dialysis, filtration, ultrafiltration, and combination thereof.

29. The method of claim 27, wherein said centrifugation is carried at below 100,000 g for a period of from about 10 minutes to about 48 hours.

30. The method of claim 27 further comprising the step of:

centrifugating said centrifugated starting supernatant at a range from about 100,000 g to about 150,000 g for a period of from about 10 minutes to about 48 hours.

31. A method of producing a Factor from aloe, said Factor being analgesic, antiviral, antiinflammatory, antineoplastic, immune stimulating, immune modulating or adjuvant, said method comprising the steps of:

filtering a bulk pharmaceutical mannan with a filter, having a pore size ranging from about 100 $\mu$m to about 800 $\mu$m, to give a filtered starting filtrate;

ultrafiltering said filtered starting filtrate to give an ultra-filtered filtrate having a molecular weight of greater than about 100 Daltons and a retentate having a molecular weight of greater than about 10,000 Daltons; and sizing said ultra-filtered filtrate with a method selected from the group consisting of irradiation, dialysis, centrifugation, ultracentrifugation, chromatography, and combination thereof.

32. The method of claim 31 further comprising the step of sizing said retentate with a method selected from the group consisting of irradiation, dialysis, centrifugation, ultracentrifugation, chromatography, and combination thereof.

33. A method of producing a Factor from aloe, said Factor being analgesic, antiviral, antiinflammatory, antineoplastic, immune stimulating, immune modulating or adjuvant, said method comprising the steps of:

sizing a bulk pharmaceutical mannan with a method selected from the group consisting of chromatography, irradiation, filtration, ultrafiltration, dialysis, centrifugation, ultracentrifugation, and combination thereof.

34. A method of producing a Factor from aloe, said Factor being analgesic, antiviral, antiinflammatory, antineoplastic, immune stimulating, immune modulating or adjuvant, said method comprising the steps of:

filtering a bulk pharmaceutical mannan with a fine filter, having a pore size ranging from about 0.04 $\mu$m to about 100 $\mu$m, to give a finely-filtered filtrate and a finely-filtered retentate; and sizing said finely-filtered filtrate with a method selected from the group consisting of chromatography, irradiation, filtration, ultrafiltration, dialysis, centrifugation, ultracentrifugation, and combination thereof.

35. The method of claim 34 further comprising the step of:

sizing said finely-filtered retentate with a method selected from the group consisting of chromatography, irradiation, filtration, ultrafiltration, dialysis, centrifugation, ultracentrifugation, and combination thereof.

36. A method of producing a Factor from aloe, said Factor being analgesic, antiviral, antiinflammatory, antineoplastic, immune stimulating, immune modulating or adjuvant, said method comprising the steps of:

filtering a bulk pharmaceutical mannan with a medium filter, having a pore size ranging from about 100 $\mu$m to about 400 $\mu$m, to give a mediumly-filtered filtrate and a mediumly-filtered retentate;

filtering said mediumly-filtered filtrate with a fine filter, having a pore size ranging from about 0.04 $\mu$m to about 100 $\mu$m, to give a finely-filtered filtrate and a finely-filtered retentate; and sizing said finely-filtered filtrate with a method selected from the group consisting of irradiation, chromatography, irradiation, filtration, ultrafiltration, dialysis, centrifugation, ultracentrifugation, and combination thereof.

37. The method of claim 36 further comprising the step of:

sizing said finely-filtered retentate with a method selected from the group consisting of irradiation, chromatography, irradiation, filtration, ultrafiltration, dialysis, centrifugation, ultracentrifugation, and combination thereof.

38. A method of producing a Factor from aloe, said Factor being analgesic, antiviral, antiinflammatory, antineoplastic, immune stimulating, immune modulating or adjuvant, said method comprising the steps of:

filtering a bulk pharmaceutical mannan with a fine filter, having a pore size ranging from about 0.04 $\mu$m to about 100 $\mu$m, to give a filtered starting filtrate;

irradiating said filtered starting filtrate with a gamma radiation in an amount from about 2 MRad to about 15 MRad to give a filtered and irradiated Factor; and centrifugating said filtered and irradiated Factor at a range from about 1 g to about 20,000 g for a period of from about 10 minutes to about 48 hours to give first pellet Factor and a first supernatant Factor.

39. The method of claim 38 further comprising the step of ultracentrifugating the first supernatant Factor at above about 20,000 g for a period of from about 10 minutes to about 48 hours to give second pellet Factor and a second supernatant Factor.

40. The method of claim 38 further comprising the step of:
sizing said first supernatant Factor with a method selected from the group consisting of centrifugation, ultracentrifugation, chromatography, irradiation, filtration, ultrafiltration, dialysis, and combination thereof.

41. The method of claim 38 further comprising the step of:
sizing said first pellet Factor with a method selected from the group consisting of centrifugation, ultracentrifugation, chromatography, irradiation, filtration, ultrafiltration, dialysis, and combination thereof.

42. A method of producing a Factor from aloe, said Factor being analgesic, antiviral, antinflammatory, antineoplastic, immune stimulating, immune modulating or adjuvant, said method comprising the steps of:
filtering a bulk pharmaceutical mannan with a filter, having a pore size ranging from about 25 µm to about 100 µm, to give a filtered starting filtrate;
irradiating said filtered starting filtrate with a gamma radiation in an amount from about 2 MRad to about 15 MRad to give a filtered and irradiated Factor; and
step-wise filtering said filtered and irradiated Factor with filters having pore size smaller than about 25 µm to give a filtrate Factor and a retentate Factor.

43. The method of claim 42 further comprising the step of:
sizing said filtrate Factor with a method selected from the group consisting of centrifugation, ultracentrifugation, chromatography, irradiation, filtration, ultrafiltration, dialysis, and combination thereof.

44. The method of claim 42 further comprising the step of:
sizing said retentate Factor with a method selected from the group consisting of centrifugation, ultracentrifugation, chromatography, irradiation, filtration, ultrafiltration, dialysis, and combination thereof.

45. The method of claim 42 further comprising the step of:
filtering said filtrate Factor using a filter, having a pore size ranging from about 5 µm to about 25 µm, giving a first retentate Factor and a first filtrate Factor.

46. The method of claim 45 further comprising the step of:
filtering said first filtrate Factor using a filter, having a pore size ranging from about 1 µm to about 5 µm, to give a second retentate Factor and a second filtrate Factor.

47. The method of claim 46 further comprising the step of:
filtering said second filtrate Factor using a filter, having a pore size ranging from about 0.1 µm to about 1 µm, to give a third retentate Factor and a third filtrate Factor.

48. The method of claim 47 further comprising the step of:
filtering said third filtrate Factor using a filter, having a pore size ranging from about 0.04 µm to about 0.1 µm, to give a fourth retentate Factor and a fourth filtrate Factor.

49. A method of producing a bioactive Factor comprising the step of compounding at least a first Factor from aloe with a second compound or mixture of compounds from aloe.

50. A method of producing a therapeutic composition comprising the step of mixing a Factor from aloe, said Factor being analgesic, antiviral, antinflammatory, antineoplastic, immune stimulating, immune modulating or adjuvant, with a known pharmaceutical agent.

* * * * *

UNITED STATES PATENT AND TRADEMARK OFFICE
CERTIFICATE OF CORRECTION

PATENT NO. : 5,902,796
DATED : May 11, 1999
INVENTOR(S) : Shand, et al

It is certified that error appears in the above-identified patent and that said Letters Patent is hereby corrected as shown below:

Col. 15, line 20, "was" should be --wash--.

Col. 18, line 23, "14S" should be --148--.

Signed and Sealed this

Fourth Day of January, 2000

Attest:

*Attesting Officer*            *Acting Commissioner of Patents and Trademarks*